US009125598B2

(12) United States Patent
Makihira et al.

(10) Patent No.: US 9,125,598 B2
(45) Date of Patent: Sep. 8, 2015

(54) OPTICAL COHERENCE TOMOGRAPHY APPARATUS, CONTROL METHOD, AND COMPUTER-READABLE STORAGE MEDIUM

(71) Applicant: CANON KABUSHIKI KAISHA, Tokyo (JP)

(72) Inventors: Tomoyuki Makihira, Tokyo (JP); Makoto Sato, Tokyo (JP); Kazuhide Miyata, Yokohama (JP); Yoshihiko Iwase, Kyoto (JP); Kazuro Yamada, Kawasaki (JP); Ritsuya Tomita, Kawasaki (JP); Yohei Minatoya, Yokohama (JP); Daisuke Kibe, Chigasaki (JP); Hiroyuki Shinbata, Tama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/855,526

(22) Filed: Apr. 2, 2013

(65) Prior Publication Data

US 2013/0293838 A1 Nov. 7, 2013

(30) Foreign Application Priority Data

Apr. 3, 2012 (JP) ................................ 2012-084969

(51) Int. Cl.

| | |
|---|---|
| ***A61B 3/14*** | (2006.01) |
| ***A61B 3/00*** | (2006.01) |
| ***G01N 21/47*** | (2006.01) |
| ***A61B 3/10*** | (2006.01) |
| *G01N 21/17* | (2006.01) |

(52) U.S. Cl.

CPC . *A61B 3/14* (2013.01); *A61B 3/102* (2013.01); *G01N 21/4795* (2013.01); *G01N 2021/1787* (2013.01)

(58) Field of Classification Search

USPC ................................................ 351/200–246

See application file for complete search history.

(56) References Cited

U.S. PATENT DOCUMENTS

| | | | | |
|---|---|---|---|---|
| 5,321,501 A | 6/1994 | Swanson | | |
| 7,980,696 B1 | 7/2011 | Taki et al. | .................... | 351/206 |
| 8,115,934 B2 * | 2/2012 | Boppart et al. | ............... | 356/479 |
| 8,556,424 B2 * | 10/2013 | Iwase et al. | ................... | 351/206 |

(Continued)

FOREIGN PATENT DOCUMENTS

JP 2008-154941 A 7/2008

OTHER PUBLICATIONS

Non-final Office Action of U.S. Appl. No. 13/855,497, dated Dec. 15, 2014.

(Continued)

*Primary Examiner* — Mohammed Hasan

(74) *Attorney, Agent, or Firm* — Canon USA, Inc., IP Division

(57) ABSTRACT

Provided is an optical coherence tomography apparatus for obtaining a tomographic image from an interference light between a reference light and a measurement light having passed through an object. The optical coherence tomography apparatus includes: a storage unit for storing information of a display mode of an imaging screen when the object is imaged; and a control unit for displaying an imaging screen of a display mode, based on the information stored in the imaging, as an initial screen, when the object is imaged after storage in the storage unit.

20 Claims, 15 Drawing Sheets

(56) References Cited

U.S. PATENT DOCUMENTS

| | | | | |
|---|---|---|---|---|
| 8,687,201 | B2 * | 4/2014 | Adler | 356/497 |
| 2013/0194094 | A1 | 8/2013 | Nakahara et al. | 351/208 |

OTHER PUBLICATIONS

Final Office Action of U.S. Appl. No. 13/855,497, dated May 13, 2015.

* cited by examiner

OPTICAL COHERENCE TOMOGRAPHY APPARATUS, CONTROL METHOD, AND COMPUTER-READABLE STORAGE MEDIUM

BACKGROUND OF THE INVENTION

1. Field of the Invention

The present invention relates to an optical coherence tomography (OCT) apparatus, and an OCT apparatus control method.

2. Description of the Related Art

An eye portion tomographic image capturing apparatus such as an OCT (Optical Coherence Tomography) can three-dimensionally observe the state inside a tissue, for example, a retinal layer. An example of the OCT is a TD-OCT (Time domain OCT) that is a combination of a broadband light source and a Michelson interferometer. The TD-OCT obtains depth resolution information by measuring an interference light between a backscattered light of a reference arm and a backscattered light of a signal arm while changing an optical path of the reference arm. Also, there is known an SD-OCT (Spectral domain OCT) that uses a spectroscope instead of changing an optical path of a reference arm, detects a dispersed light by a line sensor, and acquires an interferogram. Also, there is known an SS-OCT (Swept Source OCT) based on a technique that measures a spectral interference by a single-channel photodetector by using a high-speed wavelength-swept light source as a light source (U.S. Pat. No. 5,321,501). The OCT has been developed as described above, and development is being conducted to image a plurality of areas by a single device. For example, the department of ophthalmology is beginning to image an anterior eye portion and a posterior eye portion by a single device.

In the OCT, as an optical path length difference between a reference light and a measurement light becomes smaller, that is, as an optical path length becomes closer to the same position (coherence gate position), a better image quality is obtained. It has been known that discloses changing the optical path length difference between a reference light and a measurement light according to an SN of an image (Japanese Patent Application Laid-Open No. 2008-154941).

However, when a plurality of areas is imaged, since an imaging screen is not always suitable for a target to be imaged, rapid imaging is impossible.

SUMMARY OF THE INVENTION

Therefore, in order to solve the above problem, an exemplary object of the present invention is to rapidly set an imaging screen in OCT imaging.

Further features of the present invention will become apparent from the following description of exemplary embodiments (with reference to the attached drawings).

DESCRIPTION OF THE EMBODIMENTS

Embodiments of the present invention will be described in detail with reference to the drawings.

[Overall Configuration of Apparatus]

Figure 1:
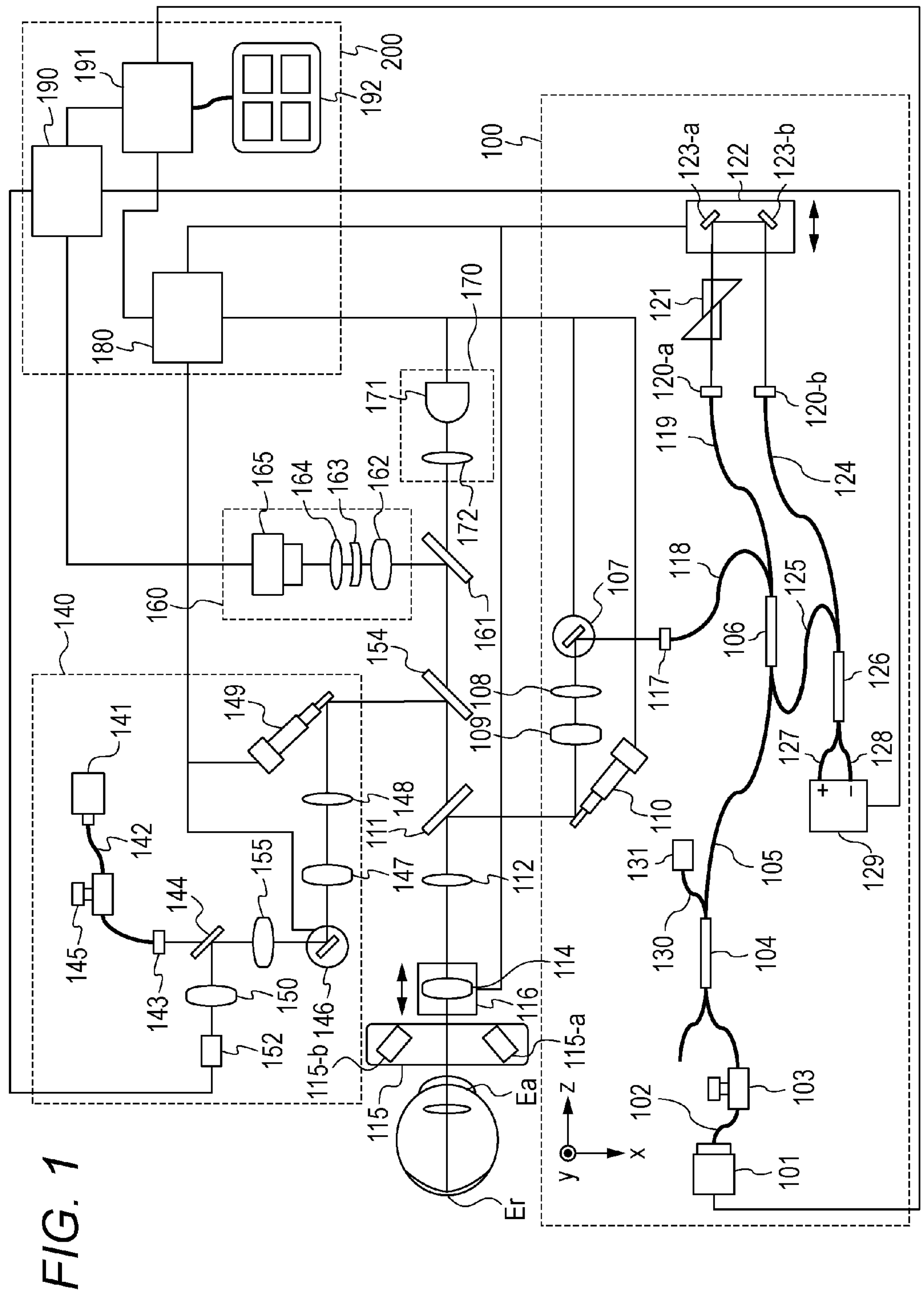
FIG. 1 is a schematic diagram of an overall configuration of an OCT apparatus according to the present embodiment.

FIG. 1 is a diagram illustrating a configuration of an OCT (Optical Coherence Tomography) apparatus according to the present embodiment. The OCT apparatus according to the present embodiment is an OCT apparatus that splits a light from a wavelength-swept light source into a reference light and a measurement light passing through an object and obtains a tomographic image from an interference light between these two light fluxes. The OCT apparatus according to the present embodiment includes an SS-OCT (Swept Source OCT; hereinafter referred to as OCT) 100, a Scanning Laser Ophthalmoscope (hereinafter referred to as SLO) 140, an anterior eye portion image capturing unit 160, an internal fixation lamp 170, and a control unit 200.

The internal fixation lamp 170 is turned on and focused on an examinee eye, and an image of an anterior eye portion of the examinee eye observed by the anterior eye portion image capturing unit 160 is used to perform an alignment of the apparatus. After completion of the alignment, an image of an eye fundus is captured by the OCT 100 and the SLO 140.

<Configuration of OCT 100>

The OCT 100 functions as an imaging unit that captures a tomographic image by scanning a region of the target to be imaged of the examinee eye with the light from the wavelength-swept light source. A configuration of the OCT 100 will be described.

A light source 101 is a wavelength-swept light source capable of changing a wavelength, and emits, for example, a light with a center wavelength of 1040 nm and a bandwidth of 100 nm. The light emitted from the light source 101 is guided through a fiber 102 and a polarization controller 103 to a fiber coupler 104, and is branched into a fiber 130 measuring a light quantity and a fiber 105 measuring an OCT. The light emitted from the light source 101 passes through the fiber 130, and the power thereof is measured by a PM (Power Meter) 131. The light having passed through the fiber 105 is guided to a second fiber coupler 106. The fiber coupler 106 functions as a splitting unit that splits an optical path, through which the light from the light source 101 is transmitted, into an optical path of reference light and an optical path of measurement light. Accordingly, the light from the light source is branched into the measurement light (also referred to as OCT measurement light) and the reference light. The polarization controller 103 adjusts a polarization state of the light emitted from the light source 101, into a linear polarization. A branching ratio of the fiber coupler 104 is 99:1, and a branching ratio of the fiber coupler 106 is 90 (reference light):10 (measurement light).

The measurement light branched by the fiber coupler 106 is emitted as a parallel light through a fiber 118 from a collimator 117. The emitted measurement light arrives at a dichroic mirror 111 through an X scanner 107 including a galvano mirror scanning an eye fundus Er with measurement light in a horizontal direction, lenses 108 and 109, and a Y scanner 110 including a galvano mirror scanning the eye fundus Er with the measurement light in a vertical direction. The X scanner 107 and the Y scanner 110 are controlled by a driving control unit 180, and can scan a desired range of area in the eye fundus Er with the measurement light. The dichroic mirror 111 has the property of reflecting a light of 950 nm to 1100 nm and transmitting other lights.

The measurement light reflected by the dichroic mirror 111 passes through a lens 112 and arrives at a focus lens 114 mounted on a stage 116. In an imaging mode of performing tomography of a retinal layer of the eye fundus, the measurement light at the focus lens 114 is focused on the retinal layer of the eye fundus Er through an anterior eye portion Ea of an eye that is an object to be examined. The measurement light irradiating the eye fundus Er is reflected/scattered at each retinal layer, and returns to the fiber coupler 106 through the above-described optical path. The measurement light from the eye fundus Er arrives at a fiber coupler 126 from the fiber coupler 106 through a fiber 125. In an imaging mode of performing tomography of the anterior eye portion, a focusing position is adjusted to a predetermined region of the anterior eye portion, not the eye fundus. The focus adjustment to the anterior eye portion may be performed by moving the position of the focus lens 114, or the focus position can be adjusted by inserting an optical member such as a dedicated lens into the optical path before/after the focus lens 114. In this case, the optical member can be inserted/evacuated into/from the optical path by a driving unit. When an anterior eye portion imaging mode is selected, the driving unit inserts the optical member into the optical path, and when an eye fundus imaging mode is selected, the driving unit evacuates the optical member from the optical path.

On the other hand, the reference light branched by the fiber coupler 106 is emitted as a parallel light through a fiber 119 from a collimator 120-*a*. The emitted reference light is reflected through a dispersion compensating glass 121 by reference mirrors 123-*a* and 123-*b* on a coherence gate stage 122, and arrives at the fiber coupler 126 through a collimator 120-*b* and a fiber 124. Herein, an optical system from the fiber coupler 106 to the reference mirrors 123-*a* and 123-*b* is configured as a reference optical system.

The coherence gate stage 122 functions as a changing unit changing the positions of the reference mirrors 123-*a* and 123-*b*, and adjusts the optical path length of a measurement light and the optical path length of a reference light by this function. The mirror 123 is disposed such that the optical path length of the measurement light and the optical path length of the reference light are equal in the vicinity of the target to be imaged. The coherence gate stage 122 is controlled by the driving control unit 180 in order to cope with a difference in the axial length of the examinee eye or the like. The control by the driving control unit 180 will be described later.

The fiber coupler 126 functions as a wave coupling unit that couples the reference light having passed through the optical path of reference light and the measurement light having passed through the optical path of measurement light. Accordingly, the measurement light and the reference light having arrived at the fiber coupler 126 are coupled into an interference light, and an interference signal is converted into an electric signal by a balanced receiver 129 that is a photodetector detecting a coupled light through fibers 127 and 128. The obtained electric signal is analyzed by a signal processing unit 190.

<Configuration of SLO 140>

A configuration of the SLO 140 will be described.

A light source 141 is a semiconductor laser, and emits, for example, a light with a center wavelength of 780 nm in the present embodiment. A measurement light emitted from the light source 141 (also referred to as an SLO measurement light) passes through a fiber 142, is adjusted to a liner polarization by a polarization controller 145, and is emitted as a parallel light from a collimator 143. The emitted measurement light passes through a perforated portion of a perforated mirror 144, passes through a lens 155, passes through an X scanner 146 including a galvano mirror scanning the eye fundus Er with a measurement light in the horizontal direction, lenses 147 and 148, and a Y scanner 149 including a galvano mirror scanning the eye fundus Er with the measurement light in the vertical direction, and arrives at a dichroic mirror 154. The X scanner 146 and the Y scanner 149 are controlled by the driving control unit 180, and can scan a desired range on the eye fundus with the measurement light. The dichroic mirror 154 has the property of reflecting a light of 760 nm to 800 nm and transmitting other lights.

The linearly-polarized measurement light reflected by the dichroic mirror 154 transmits through the dichroic mirror 111, passes through the same optical path as the OCT measurement light of the OCT 100, and arrives at the eye fundus Er.

The SLO measurement light irradiating the eye fundus Er is reflected/scattered at the eye fundus Er and arrives at the perforated mirror 144 along the above-described optical path. The light reflected by the perforated mirror 144 passes through a lens 150, is received by an avalanche photodiode (hereinafter referred to as APD) 152, is converted into an electric signal, and is received by the signal processing unit 190.

Herein, the position of the perforated mirror 144 is conjugated with the position of a pupil of the examinee eye, and the light having passed through a peripheral portion of the pupil, among the light resulting from the reflection/scattering of the measurement light irradiated on the eye fundus Er, is reflected by the perforated mirror 144.

<Anterior Eye Portion Image Capturing Unit 160>

The anterior eye portion image capturing unit 160 will be described.

The anterior eye portion image capturing unit 160 irradiates the anterior eye portion Ea by an illumination light source 115 including LEDs 115-*a* and 115-*b* emitting a light with a wavelength of 850 nm. The light reflected by the anterior eye portion Ea passes through the focus lens 114, the lens 112 and the dichroic mirrors 111 and 154, and arrives at a dichroic mirror 161. The dichroic mirror 161 has the property of reflecting a light of 820 nm to 900 nm and transmitting other lights. The light reflected by the dichroic mirror 161 passes through lenses 162, 163 and 164 and is received by an anterior eye portion camera 165. The light received by the anterior eye portion camera 165 is converted into an electric signal, and the electric signal is received by the signal processing unit 190.

<Internal Fixation Lamp 170>

The internal fixation lamp 170 will be described.

The internal fixation lamp 170 includes a display unit 171 and a lens 172. The display unit 171 includes a plurality of light emitting diodes (LD) disposed in a matrix configuration. The turn-on position of the light emitting diode is changed in accordance with a region desiring to be imaged by the control of the driving control unit 180. The light from the display unit 171 is guided through the lens 172 to the examinee eye. The light emitted from the display unit 171 is 520 nm, and a desired pattern thereof is displayed by the driving control unit 180.

<Image Processing>

Next, the image generation and image analysis in the signal processing unit 190 will be described.

<Tomographic Image Generation and Eye Fundus Image Generation>

The signal processing unit 190 generates a tomographic image by performing general reconstruction processing on each interference signal output from the balanced receiver 129.

First, the signal processing unit 190 removes a fixed pattern noise from the interference signal. The fixed pattern noise is extracted by averaging a plurality of A scan signals detected, and the fixed pattern noise is removed by subtracting the fixed pattern noise from the input interference signal.

Next, the signal processing unit 190 performs desired window function in order to optimize a depth resolution and a dynamic range that are in a trade-off relation when Fourier-transformed in a finite interval. Next, FFT processing is performed to generate a tomographic signal.

<Imaging Mode Switching>

Figure 2A:
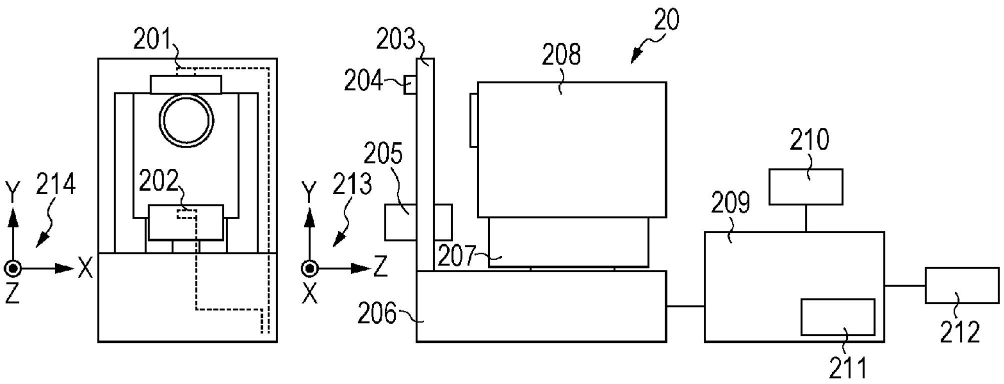
FIGS. 2A-2B are diagrams illustrating an external appearance of an OCT apparatus.
Figure 2B:
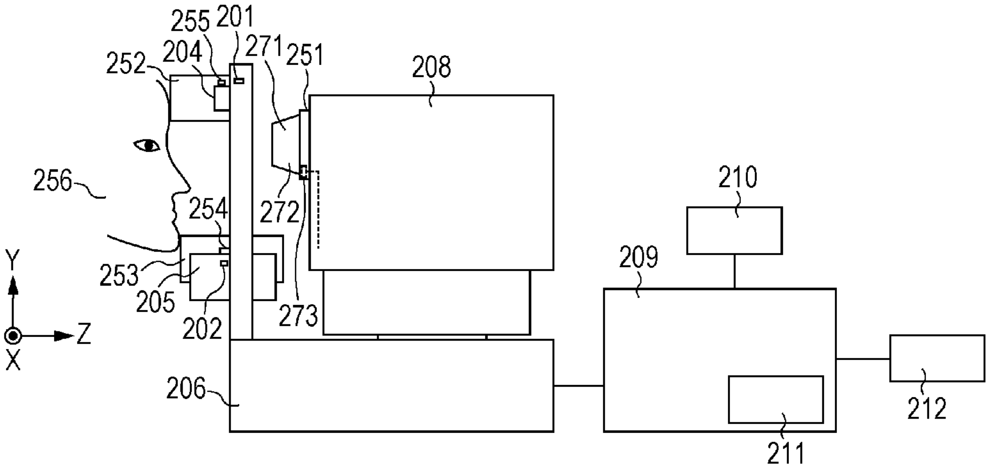

The switching of the imaging modes of the anterior eye portion and the posterior eye portion will be described based on the external appearance diagram of FIG. 2 (FIGS. 2A-2B). In FIG. 2A, an OCT apparatus 20 is divided into a plurality of physical units. Since the OCT 100 can be used to image a long-wavelength light by using a variable-wavelength light source, the OCT 100 is suitable for imaging not only a thin target such as a retina at an eye fundus but also a relatively thick target such as an anterior eye portion. Also, since sensitivity reduction can be suppressed even when the optical path difference between the SS-OCT measurement light and the reference light becomes larger, the OCT 100 is suitable for imaging a thick target. By using this property, both the anterior eye portion and the posterior eye portion can be imaged by the SS-OCT.

Figure 11:
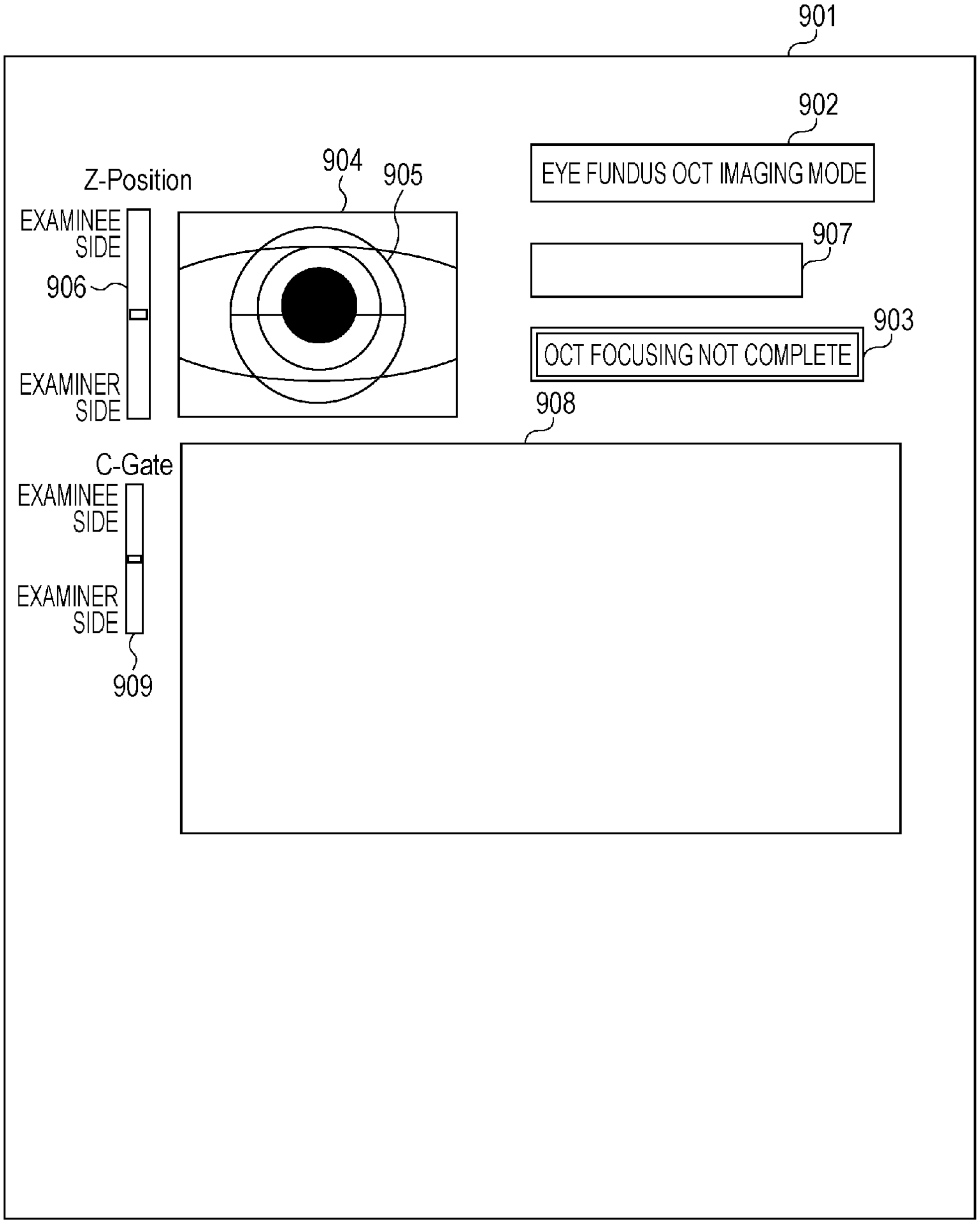
FIG. 11 is a diagram illustrating an example of an imaging screen in the case of eye fundus imaging.
Figure 12:
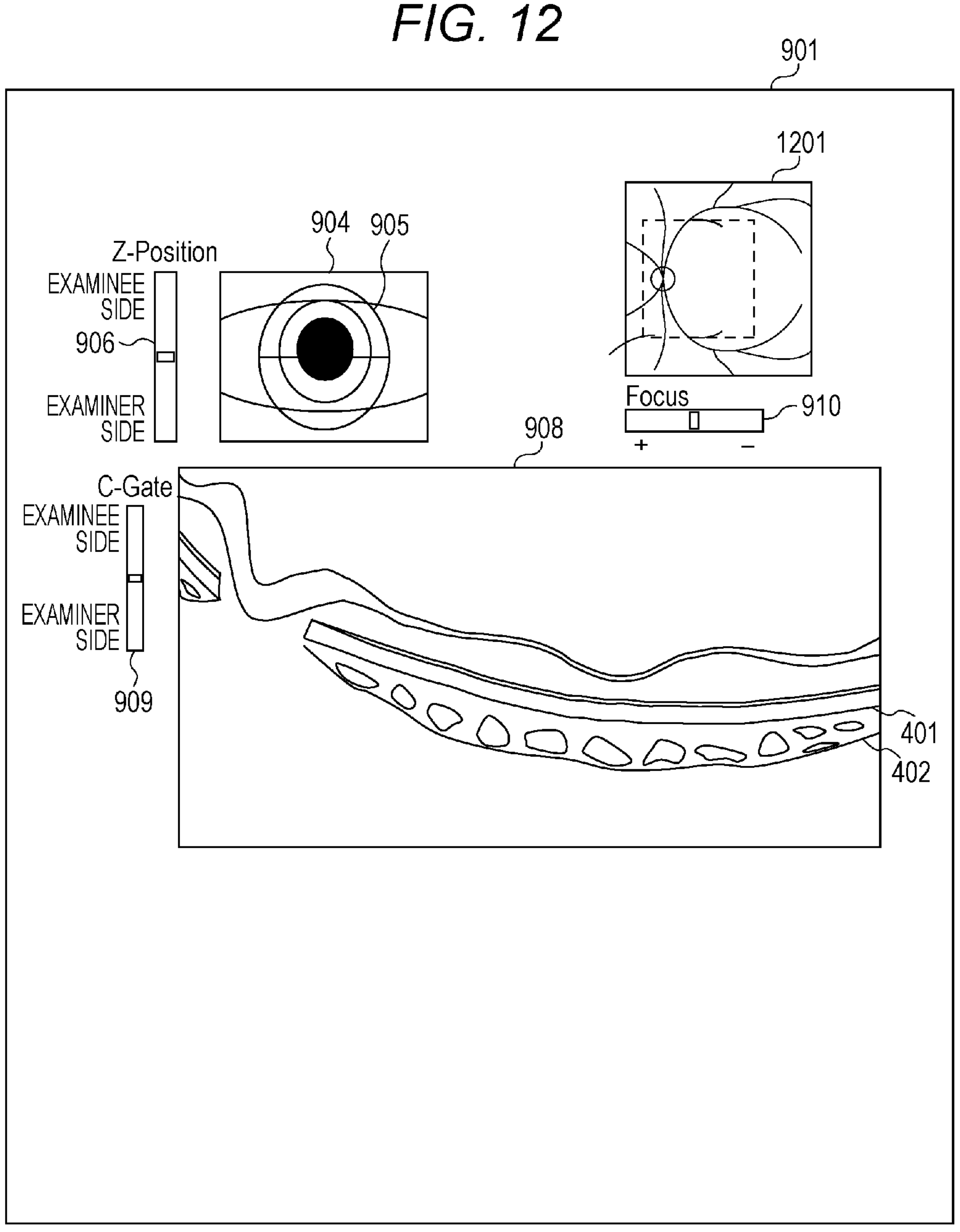
FIG. 12 is a diagram illustrating another example of an imaging screen in the case of eye fundus imaging.
Figure 13:
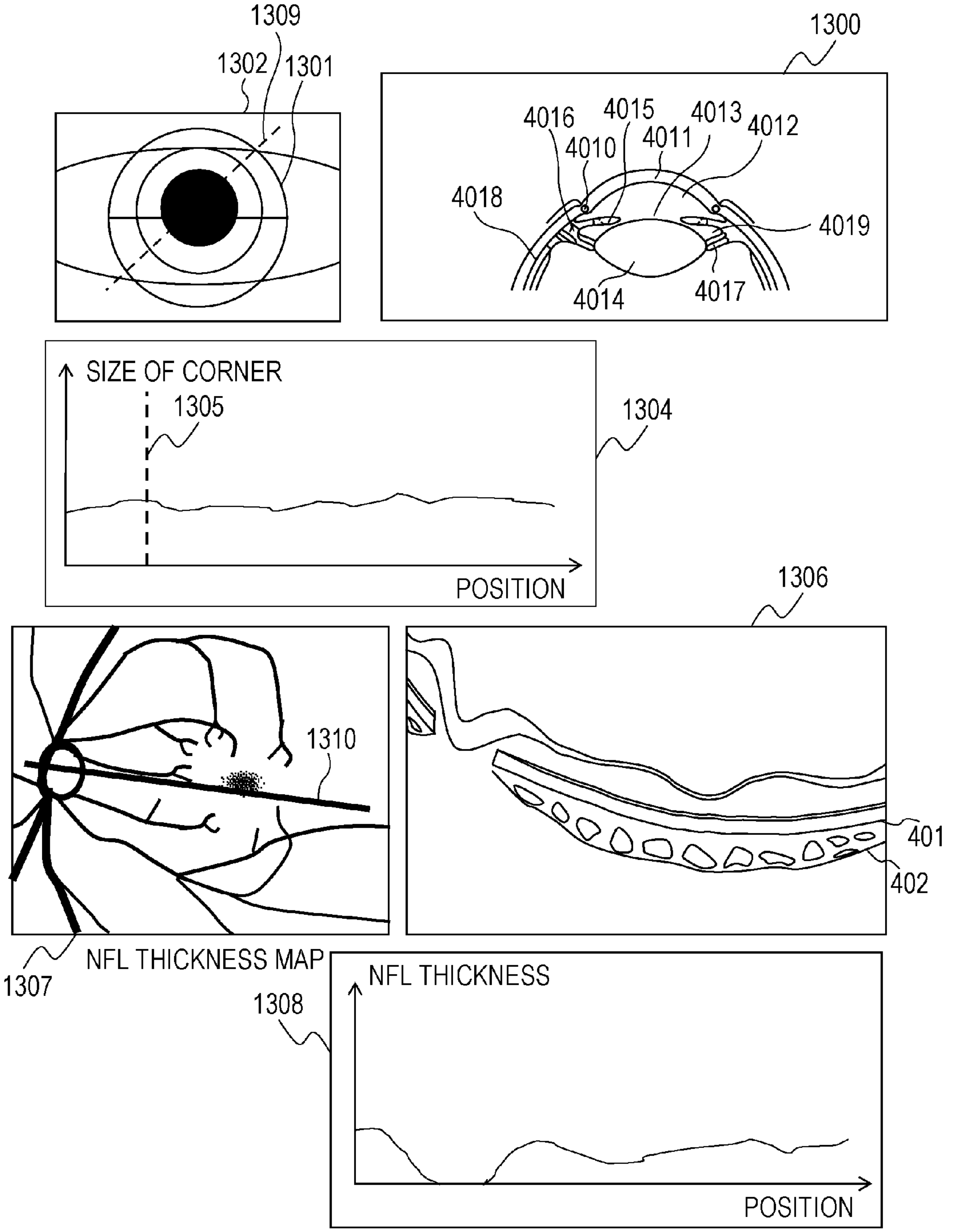
FIG. 13 is a diagram illustrating an example of a display screen of analysis results.

Therefore, an imaging screen is switched according to the imaging modes of the anterior eye portion and the posterior eye portion. For example, imaging screens of FIGS. 9 and 10 described later are used in the case of the anterior eye portion, and imaging screens of FIGS. 11, 12 and 13 are used in the case of the posterior eye portion. A screen displaying the tomographic image of the imaging screen for the anterior eye portion is smaller than a screen displaying the tomographic image of the imaging screen for the posterior eye portion in terms of the ratio of a horizontal-direction display range to a depth-direction display range.

In the OCT apparatus 20 illustrated in FIG. 2A, an optical head 208 is a measurement optical system for acquiring an anterior eye image, a tomographic image and a two-dimensional image of the eye fundus, and a stage unit 207 is a moving unit that can move the optical head 208 in XYZ directions by using a motor (not illustrated). The stage unit 207 functions as an alignment unit that changes the distance/position relation between the examinee eye and the OCT apparatus 20. A base unit 206 has an embedded spectroscope that will be described later. A personal computer 209 serves also as a control unit of the stage unit 207, and performs control of the stage unit 207, construction of a tomographic image, and the like, which will be described later. A hard disk 211 stores an examinee information storage unit, a test set storage unit, a tomography program, and the like. A monitor 210 is a display unit. An input unit 212 issues an instruction to the personal computer 209. Specifically, the input unit 212 includes a keyboard and a mouse. A face receiver 203 fixes the chin and forehead of the examinee, thereby facilitating the fixation of the eye of the examinee. A silicon rubber member 204 receives the forehead of the examinee (hereinafter referred to as forehead guard). A chin receiving member 205 receives the chin of the examinee (hereinafter referred to as chin receiver). The chin receiving member 205 is operated by an actuator (not illustrated) at a 30 mm stroke in the Y-axis direction, and adjusts the height of the examinee eye. A Hall element 201 is attached inside an upper case of an attachment portion of the forehead guard silicon rubber member 204. Also, a Hall element 202 is attached inside the chin receiving member 205. The Hall elements 201 and 202 are connected to a CPU substrate (not illustrated) installed in an ophthalmologic test apparatus 200, and are configured to detect magnetism.

Also, the chin receiver receiving the chin of the examinee, or the forehead receiver (forehead guard) receiving the forehead of the examinee is an embodiment of the attachment member in the present invention, and at least one of the chin receiver and the forehead receiver may be used. Also, the attachment members are attached to the ophthalmologic apparatus to move the focus of the ophthalmologic apparatus to an anterior eye portion.

FIG. 2B illustrates an example of an OCT apparatus with an anterior eye portion imaging adapter attached thereto. A reference numeral 251 denotes an object lens barrel. A member 252 is configured to adjust a focus position to the anterior eye portion of an examinee 256 (hereinafter, the member 252 will be referred to as an attachment forehead guard). The attachment forehead guard 252 is formed of silicon rubber. A reference numeral 255 denotes a magnet. The magnet 255 is embedded in the attachment forehead guard 252, which is attached to the face receiver 203 in such a way as to cover the forehead guard 204. A surface fastener or an attachment mechanism (not illustrated) is provided such that the magnet 255 is not detached from the face receiver 203. When the attachment forehead guard 252 is attached to the face receiver 203 in such a way as to cover the forehead guard 204, the Hall element 201 reacts to magnetism. Then, a CPU (not illustrated) installed in the ophthalmologic test apparatus 200 detects that the attachment forehead guard 252 is attached to the main body. A member 253 is configured to adjust a focus position to the anterior eye portion of the examinee 256 (hereinafter, the member 253 will be referred to as an attachment chin guard). The attachment chin guard 253 is formed of silicon rubber. A reference numeral 254 denotes a magnet. The magnet 254 is embedded in the attachment chin guard 253, and is attached to the chin receiver 205 in such a way as to be covered by the chin guard 253. When the attachment chin guard 253 covers the chin receiver 205, the Hall element 202 reacts to magnetism. Then, a CPU (not illustrated) installed in the OCT apparatus 20 detects that the attachment chin guard 253 is attached to the chin receiver 205. A reference numeral 271 denotes a barrel in which an anterior eye imaging lens is embedded. Therefore, in this case, as an attachment member, an optical member attached before an object lens is also included. The object lens barrel 251 is squeezed into a filter screw portion (not illustrated) to be attached to the OCT apparatus 20. A reference numeral 272 denotes a magnet. The magnet 272 is embedded in the vicinity of the filter screw portion of the barrel 271. A reference numeral 273 denotes a Hall element. The Hall element 273 is electrically connected to the CPU (not illustrated) installed in the OCT apparatus 20. When squeezed into the filter screw portion (not illustrated) of the object lens barrel 271 to be attached to the OCT apparatus 20, the Hall element 273 reacts to the magnet 272. Then, the CPU (not illustrated) installed in the OCT apparatus 20 detects that the barrel 271 is attached to the OCT apparatus 20. Although it has been illustrated above that the Hall elements are used to detect the anterior eye imaging attachment members 252, 253 and 271, a capacitive distance sensor or a switch-type sensor may also be used to detect the attachment.

Also, a sensor such as a Hall element for determining the attachment/detachment of the attachment member attached to the ophthalmologic test apparatuses, and a CPU actually determining the attachment/detachment based on a signal obtained from the sensor, or a determination module area in the personal computer 209 cooperatively function as an attachment detecting unit for detecting the attachment state of an anterior eye portion imaging adapter member. Also, the attachment detecting unit determines whether an anterior eye portion imaging mode is selected by an imaging mode selecting unit that will be described later. Also, as the attachment member of the present invention, the optical member attached to the examinee eye side of the object lens on the optical path of the measurement light is illustrated as an embodiment thereof. The attachment detecting unit always monitors the detection of attachment/detachment, and the attachment/detachment detection result is notified to the control unit 200. The detection result is notified whenever there is a change in the detection result.

By the above-described configuration, the attachment/detachment of the anterior eye portion imaging adapter unit can be automatically detected. When a tomographic image is captured, the tomographic image, a two-dimensional image of the anterior eye portion or the eye fundus, capturing position information of the tomographic image, imaging region information, examinee ID information, imaging time information, imaging screen information, optical path length difference (coherence gate) information, and information about the presence/absence of an eye imaging attachment member are associatively stored in the examinee information storage unit 211.

<Control Unit 200>

A detailed configuration of the control unit 200 will be described based on FIG. 3. Respective control units described below are controlled by the control unit 200.

The control unit 200 includes a CG (Coherence Gate) control unit 301 that controls the optical path length difference (coherence gate) between the reference light and the measurement light by a control method according to an imaging region. In this case, when there is information stored in the examinee information storage unit 211, an imaging screen according to the examinee and a CG (Coherence Gate) are set as information.

In this case, the imaging position of a tomographic image captured in the past is also displayed. Examples of the imaging position include a line 1003 of FIG. 10 and lines 1301 and 1301 of FIG. 13, which will be described later. Also, a two-dimensional image of the anterior eye portion is displayed in the case of the anterior eye portion, and an eye fundus image is displayed in the case of the posterior eye portion. In this manner, by using the examinee information, the imaging screen is rapidly switched. In addition, by using the previous imaging information easily, the comparison with the image captured in the past is simplified.

In addition, there is a case where signal attenuation is small and fine adjustment of a coherence gate is not necessary depending on an object, or a case where the adjustment is not necessary in the first place. Based on this property, by changing a method of controlling the optical path length difference between the reference light and the measurement light according to the information stored in the examinee information storage unit 211 and by performing control in the CG control unit 301, rapid adjustment can be implemented without wasting a time in unnecessary adjustment.

The CG control unit 301 controls the optical path length difference based on the previous imaging information based on the information stored in the examinee information storage unit 211.

When the anterior eye portion as a first imaging region (anterior eye portion) is imaged, since the attenuation of the measurement light due to the object is small, there is a case where it is not necessary to search for the appropriate position of the coherence gate. Therefore, when the optical path length difference is controlled in advance by using the value stored for each examinee and the value set for a standard examinee, there is a case where an image with a good image quality is obtained even without adaptive control. When the value set for a standard examinee is used to perform imaging, the value is initialized again, and when there is a change therein, the position of a coherence gate in imaging is initialized. Also, when the position of a coherence gate different from the standard value is initialized, the CG control unit 301 continues control even after setting the optical path length difference to the initial value.

On the other hand, when the eye fundus as a second imaging region (posterior eye portion) is imaged, since signal attenuation is large and since the thickness of an object is relatively small, the appropriate adjustment of a coherence gate is necessary. Based on this property, in the case of anterior eye portion imaging, the CG control unit 301 continues control for the adjustment of a coherence gate even after setting the optical path length difference to the prestored initial value. In this case, information representing the optical path length difference is displayed at a CG slider 909 of the imaging screen.

On the other hand, when the posterior eye portion is imaged, the CG control unit 301 continues control even when any one of the value stored for each examinee and the value set for the standard examinee is set as the initial value of a coherence gate.

The CG control unit 301 searches for the position providing an appropriate optical path length difference while moving the reference mirror 123 by controlling the coherence gate stage 122. The signal processing unit 190 generates image data of the object based on an electric signal obtained by detecting an interference light in the state where the optical path length difference is controlled by the control method according to the region. Accordingly, a posterior eye portion tomographic image with a good image quality can be obtained. By the CG control unit 301, rapid imaging and good-quality image acquisition can be achieved at the same time. In particular, when the examinee eye is imaged, forcing the examinee to fix an eye for a long time is burdensome, and there is a large demand for reduction of an imaging adjustment time. The omission of adjustment is to meet this demand. Also, by reduction of an imaging cycle, the medical efficiency can be improved.

In order to search for the optical path length difference, feedback control using image information can be used. A determination unit 310 makes a movement by a predetermined length, the signal processing unit 190 acquires a tomographic image in the state of movement, and the determination unit 310 determines whether the optical path length difference between the reference light and the measurement light is appropriate. By performing control for repeating this processing, the CG control unit 301 searches for the appropriate position of the reference mirror 123, that is, the appropriate position of the optical path length difference. In this way, for search control of the appropriate optical path length difference by the CG control unit 301 in the imaging of the posterior eye portion, information of the tomographic image obtained from the signal processing unit 190 can be fed back.

Herein, the determination unit 310 can use the luminance value of the tomographic image as a criterion for determining whether the optical path length difference is appropriate. In this case, the determination unit 310 determines whether the size of a representative value of the pixel value of the image data is equal to or greater than a predetermined threshold value. The determination unit 310 acquires an average value or a median value of the entire tomographic image as a representative value of the tomographic image, and determines whether the representative value reaches a predetermined threshold value. By using the representative value, the optical path length difference can be set with high accuracy by eliminating the influence of a noise while simplifying the determination processing.

Herein, the determination unit 310 may also have a function of determining whether the adjustment of an optical path length difference by the initial value is appropriate in the case of anterior eye portion imaging. In this case, the determination unit 310 determines whether the image data obtained by the signal processing unit 190 satisfies a predetermined standard when the optical path length difference is controlled to be a predetermined value with respect to the first imaging region. When the determination unit 310 determines that the predetermined standard is not satisfied, the CG control unit 301 controls the optical path length difference based on the signal of an interference light obtained while sequentially changing the optical path length difference. That is, only when it is determined that the adjustment is not well performed by the initial value, the same search control as for the second imaging region is performed. Accordingly, the adjustment of the optical path length difference in the anterior eye portion imaging can be performed more reliably.

As for the first imaging region (anterior eye portion), by selecting the control method for performing the same adjustment as for the second imaging region (posterior eye portion), more secure adjustment can be achieved. The control method applied to the first imaging region is managed by a control setting unit 303. The correspondence relation between the imaging region and the control method is set appropriately according to the input of a user through an operation unit 312. Accordingly, the adjustment according to the preference of the user can be achieved. Also, this information is stored in the examinee information storage unit 211 and can be used for later imaging.

As an optical path length difference control method, by changing the movement distance of the reference mirror 123 during adjustment according to the imaging region, in particular, the adjustment corresponding to the thickness difference of the imaging region can be achieved. With respect to a certain imaging region, the CG control unit 301 sets the control method for determining the optical path length difference based on the signal of an interference light obtained while sequentially changing the optical path length difference at first intervals. With respect to other imaging regions, the CG control unit 301 determines the optical path length difference based on the signal of an interference light obtained while sequentially changing the optical path length difference at second intervals smaller than the first intervals. The control setting unit 303 sets a control method according to the information of the imaging region. Accordingly, the efficiency can be improved by increasing the search interval in the region where detailed search is not so required, and the accuracy can be improved by reducing the search interval in the region where detailed search is required.

Also, as another control method, with respect to a certain imaging region, the CG control unit 301 can control the optical path length difference by two-stage adjustment of coarse adjustment and fine adjustment. In this case, the CG control unit 301 performs a control method for determining a certain range of the optical path length difference based on the signal of an interference light obtained while sequentially changing the optical path length difference at certain intervals (second intervals), and determining the optical path length difference based on the signal of an interference light obtained while sequentially changing the optical path length difference within the certain range. This is a method capable of efficiently adjusting the optical path length difference with respect to a region where detailed adjustment is required, in particular, such as the posterior eye portion.

In addition, there is a control method that performs only coarse adjustment in the anterior eye portion at first intervals, and sequentially performs coarse adjustment and fine adjustment in the posterior eye region at second intervals smaller than the first intervals. Accordingly, in the anterior eye portion which is thick and does not require fine adjustment, the optical path length difference control satisfying both the efficiency and the accuracy according to the property of the anterior eye portion can be achieved. On the other hand, in the posterior eye portion which is thin and requires fine adjustment, the optical path length difference control satisfying both the efficiency and the accuracy in consideration of this property can be achieved.

With respect to both the anterior eye portion and the posterior eye portion, the CG control unit 301 can efficiently adjust the optical path length difference by using the initial value for optical path length difference control based on the information stored in the examinee information storage unit 211. In addition, more efficiency can be achieved by setting an imaging screen based on the information stored in the examinee information storage unit 211. Also, imaging in the same range can be performed by using the imaging position information of the tomographic image stored in the examinee information storage unit 211. In this case, the control unit 200 can control tomographic image capturing by using the imaging position information of the tomographic image. The X scanner 107 and the Y scanner 110 are controlled through the driving control unit 180 by using the imaging position information of the tomographic image.

In this case, in addition, the CG control unit 301 moves the reference mirror 123 sequentially from the vicinity of the position corresponding to the initial value, completes the adjustment of the optical path length difference when an image with an image quality exceeding a reference value is obtained, and stores this position corresponding to the reference mirror in a storage unit 309 and the examinee information storage unit 211. Accordingly, the search efficiency can be improved.

Also, when there is no information stored in the examinee information storage unit 211, a different initial value is set and retained with respect to each imaging region or imaging mode and an initial value according to the imaging region information is selected. Accordingly, rapid adjustment or imaging screen setting can be achieved according to each region even when there is no information stored in the examinee information storage unit 211.

When an initial value of a coherence gate and an imaging screen are set according to each examinee, the imaging efficiency can be improved even when the same examinee eye is iteratively imaged at time intervals.

As for the initial value, the optical path length difference between the reference light and the measurement light may be stored as a parameter. However, by storing the misalignment amount of the coherence gate stage 122 or the reference mirror 123 from the reference position, the high-accuracy adjustment according to the properties of these members can be achieved.

Also, the control method can be automatically set from the imaging region information. Region information is acquired by a region acquiring unit 302 according to the information stored in the examinee information storage unit 211. The acquired region information is input to the control setting unit 303. The control setting unit 303 sets a control method of the optical path length difference between the reference light and the measurement light according to the imaging region. The control setting unit 303 refers to any one of the storage unit 309 and the examinee information storage unit 211, acquires a CG control method corresponding to the acquired imaging region, and notifies the setting to the CG control unit 301. Accordingly, the CG control unit 301 can select a control method according to the region.

Also, in another example, an anterior eye portion with a relatively large thickness is used, the movement distance of the reference mirror for changing the optical path length difference can be set to be large such as not to exceed the length corresponding to the thickness of the anterior eye portion.

By associating the imaging region information with the information stored in the examinee information storage unit 211, the imaging adjustment can be rapidly executed. A mode designating unit 311 designates an imaging mode based on the information stored in the examinee information storage unit 211. Herein, the imaging mode includes setting information about a plurality of imaging operations. For example, the imaging mode includes information about imaging regions such as an anterior eye portion, a posterior eye portion, a cornea of the anterior eye portion, an optic disk of the posterior eye portion, information about a scan position of OCT default setting, and information about a scan method such as radial scan or XY scan. The region acquiring unit 302 receives imaging mode information, and extracts imaging region information corresponding to the imaging mode with reference to a lookup table of the storage unit. Accordingly, it is possible to reduce the user's trouble to perform an input operation for designating an imaging mode for each imaging region at each time through the operation unit 312.

Herein, in addition, the mode designating unit 311 can designate a continuous imaging mode for continuously imaging a plurality of imaging regions. When a target to be imaged is an eye portion, there is, for example, an imaging mode for imaging both the anterior eye portion and the posterior eye portion. In this imaging mode, after completion of the imaging of one of the anterior eye portion and the posterior eye portion, at least a portion of imaging preparation of the other one is started. Accordingly, it is possible to further reduce the user's trouble in performing an input operation for designating an imaging mode for each imaging region at each time through the operation unit 312.

In addition, the mode designating unit 311 can designate a first mode for transition to a posterior eye portion imaging mode after completion of the anterior eye portion imaging and a mode for transition to an anterior eye portion imaging mode after completion of the posterior eye portion imaging. For example, by detecting an abnormality in one region and checking a detailed situation by an image of the other region, an imaging sequence according to a diagnosis situation can be adopted.

Besides, the mode designating unit 311 can set an automatic adjustment mode indicating whether to turn off automatic adjustment.

Figure 3:
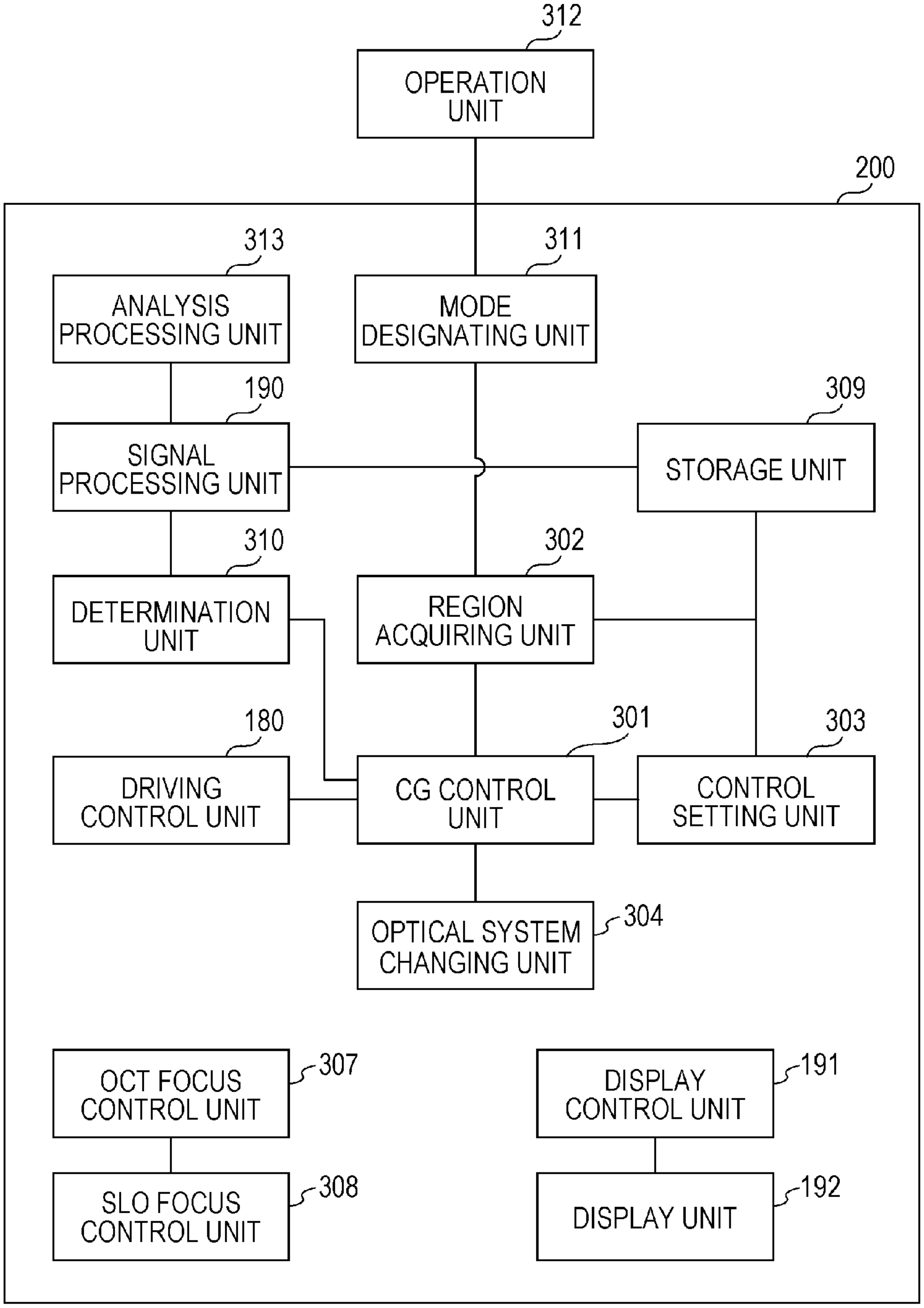
FIG. 3 is a diagram illustrating a detailed configuration of a control unit.

As illustrated in FIG. 3, the control unit 200 may include an optical system changing unit 304 that controls the driving unit capable of inserting/evacuating the anterior eye portion imaging optical system into/from the imaging optical system. When switching from anterior eye portion imaging to posterior eye portion imaging, the optical system changing unit 304 performs control to insert/evacuate an optical system (not illustrated), which is used to correct the influence caused by the passage through an optic lens, into/from an imaging path. Accordingly, when the imaging region is switched between the anterior eye portion and the posterior eye portion, the user's trouble is reduced and the imaging efficiency is improved.

Besides, the driving control unit 180 of the control unit 200 collectively controls the movement of the respective units as described above. The driving control unit 180 of the control unit 200 provides a control value for moving the coherence gate stage 122 to the driving unit, and controls the position of the coherence gate stage 122.

An OCT focus control unit 307 controls the focus position of the light from the wavelength-swept light source. An SLO focus control unit 308 controls the focus position of the measurement light of SLO.

<Segmentation>

An analysis processing unit 313 extracts useful information for diagnosis from an obtained tomographic image. For example, the analysis processing unit 313 calculates a cornea thickness or a corner size from the tomographic image of the anterior eye portion. Also, the analysis processing unit 313 extracts each layer of the retina from the tomographic image of the posterior eye portion. The analysis processing unit 313 performs segmentation of a tomographic image by using the above-described luminance image. In this case, first, the analysis processing unit 313 creates images by applying a Median filter and a Sobel filter to a tomographic image to be processed (hereinafter respectively referred to as a Median image and a Sobel image). Next, for each A scan, a profile is created from the created Median image and Sobel image. The profile is a luminance value profile in the case of the Median image, and the profile is a gradient profile in the case of the Sobel image. A peak within the profile created from the Sobel image is detected. By referring to the profile of the Median image before/after the detected peak or between the peaks, the boundary of each area of a retinal layer is detected. In addition, the thickness of each layer in the direction of an A scan line is measured, and the layer thickness map of each layer is created.

The analysis result of the analysis processing unit 313 is displayed by a display control unit 191.

The display control unit 191 displays the analysis result or the image, generated by the signal processing unit 190, on a display screen of the display unit 192. Under the control of the display control unit 191, the display unit 192 displays a variety of information as described later.

Also, the display unit 192 displays the region information acquired by the region acquiring unit 302. Accordingly, when a plurality of adjustments is automatically performed, the imaging target region can be more strongly recognized by the user, and the possibility of erroneous imaging can be reduced.

The display control unit 191 displays the attachment state of the anterior eye portion adapter unit while changing the display mode of the imaging screen according to the attachment/detachment. Herein, according to the detection of the attachment of the anterior eye portion adapter, the imaging region may be specified as the anterior eye portion. In this case, when the anterior eye portion adapter is attached, the region acquiring unit 302 automatically specifies the imaging region as the anterior eye portion.

Also, in addition, when necessary adjustment is completed and the adjustment state is incapable of appropriate imaging, the display control unit 191 performs control to display the information of the imaging target region. When the adjustment is insufficient, the display control unit 191 performs control not to display the information of the imaging target region. Herein, the determination unit 310 determines whether a tomographic image of the imaging target region has been adjusted so as to be captured by the OCT 100.

Figure 4A:
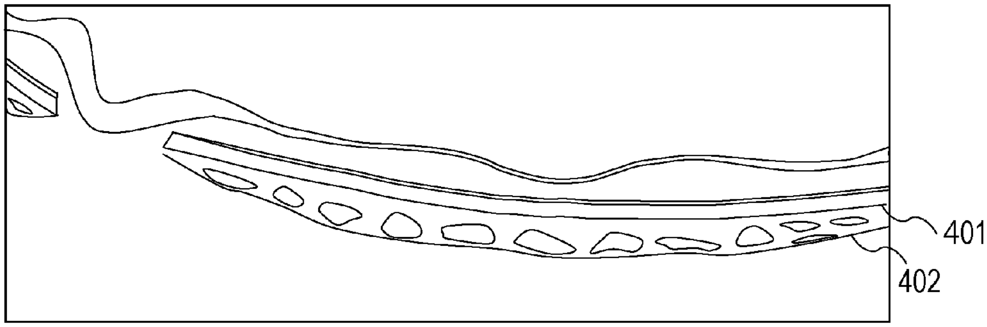
FIGS. 4A-4C are diagrams illustrating an example of a tomographic image captured by an OCT.
Figure 4B:
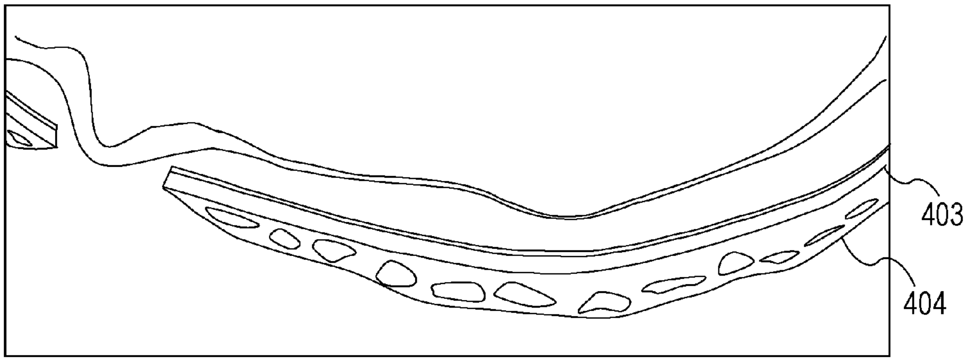
Figure 4C:
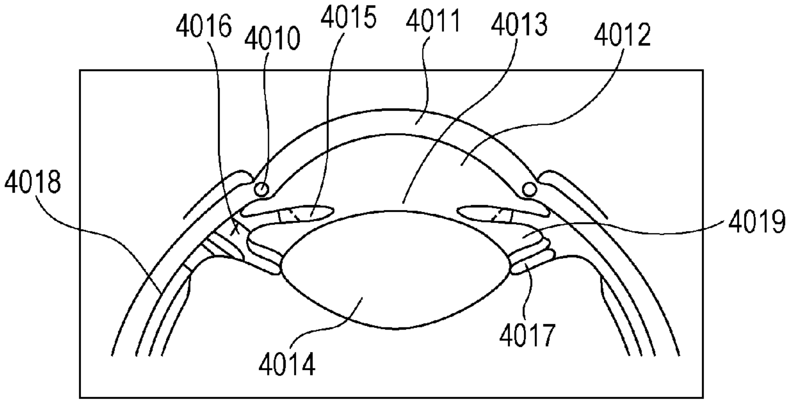

FIG. 4 (FIGS. 4A-4C) illustrates an example of a tomographic image that is captured by the OCT 100 and is generated by the signal processing unit 190.

FIG. 4A illustrates a tomographic image of a normal eye, and FIG. 4B illustrates a tomographic image of a short-sighted eye, in which a retinal pigment epithelium-choroid membrane boundary 401, a choroid membrane-sclera boundary 402, and other respective layer boundaries are imaged. As illustrated in the drawings, imaging of a tomographic image in a wide range (the size in the horizontal direction of the drawings is large), and imaging of a tomographic image deep in the depth direction (the size in the vertical direction of the drawings is large) can be implemented. Also, when the tomographic image is displayed in a display area of the display unit 192, the display of an area without a tomographic image is meaningless. Therefore, in the present embodiment, a portion of the tomographic image is recognized from the data developed on the memory in the signal processing unit 190, and a tomographic image adjusted to the size of a display area is cut out and displayed.

FIG. 4C illustrates an example of a tomographic image of an anterior eye portion obtained by imaging an examinee eye in an anterior eye portion mode. A Schlemm's canal 4010 has a plurality of small holes opened at a corner, and discharges an aqueous fluid flowing into an anterior chamber therefrom. A cornea 4011 has a light ray entrance in a transparent membrane forming an outer membrane, and functions as a lens in combination with an optic lens. An anterior chamber 4012 functions to store an aqueous fluid. The aqueous fluid is a transparent liquid that nourishes the cornea or the optic lens. The aqueous fluid is produced by a ciliary process, and functions to maintain an eye pressure. A pupil 4013 is a light entrance that is a round hole located at the center of an iris. An optic lens 4014 performs focusing in conjunction with a ciliary body. An iris 4015 has a pupil dilator and a pupil activator, and adjusts the quantity of light entering an eye by brightness/darkness.

A ciliary body 4016 fixes the iris, and performs focusing to form an image on the retina by changing the thickness of the optic lens by the tension/relaxation of a ciliary muscle. Also, the ciliary body 4016 produces an aqueous fluid. A Zinn's zonule (ciliary zonule) 4017 functions to connect the ciliary body and the optic lens and support the optic lens. A choroid membrane 4018 is abundant in ciliary blood vessel and pigment, functions to nourish the retina, and functions as a camera darkroom. Like the anterior chamber, a posterior chamber 4019 functions to store an aqueous fluid.

[Processing Operation]

Figure 5:
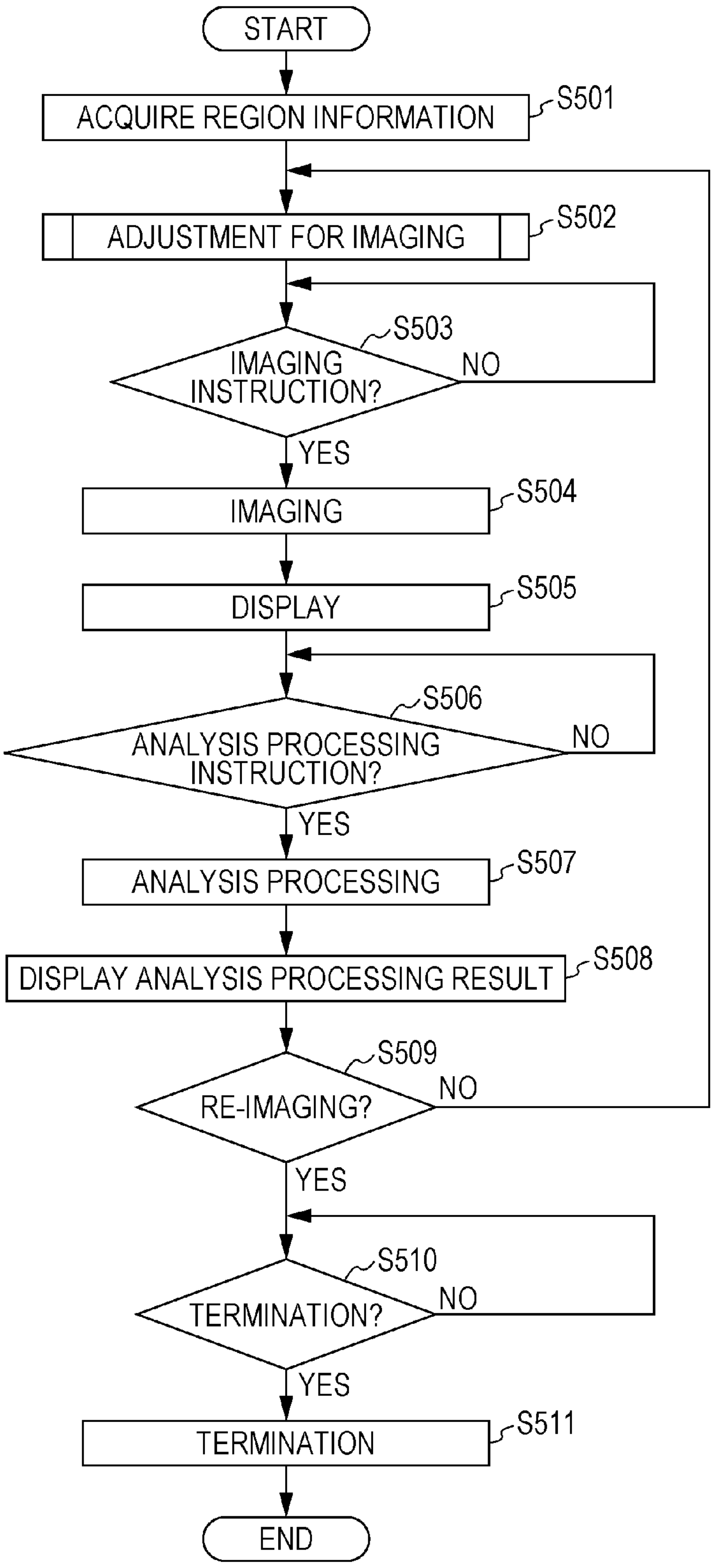
FIG. 5 is a flowchart illustrating a processing flow of an OCT apparatus.

OCT control processing using the OCT apparatus will be described with reference to the flowchart of FIG. 5.

In step S501, the region acquiring unit 302 acquires an imaging target region. Herein, the imaging region is acquired with reference to imaging mode information designated by the mode designating unit 311 according to the information stored in the examinee information storage unit 211. Then, an imaging screen corresponding to the imaging region is displayed. In this case, as described above, imaging position information and a two-dimensional image stored in the examinee information storage unit 211 are also displayed.

In step S502, adjustment processing necessary for imaging is performed. While an examinee eye is disposed in the present apparatus, alignment of the present apparatus and the examinee eye, adjustment of measurement light focus position, and the like are performed. Also, the CG control unit 301 controls the optical path length difference between the reference light and the measurement light by a control method according to the imaging region. These adjustments may be performed only by automatic adjustment using feedback control based on an image as described above, or only by manual adjustment. Alternatively, when a configuration is provided such that the result of automatic adjustment can be manually adjusted as necessary, it can be adjusted to a state that is efficient and is desired by the user. The processing of step S502 will be described in detail later.

In step S503, after completion of the adjustment, imaging instruction waiting processing is performed. The control unit 200 waits until the user operates the operation unit 312 and an input indicating an imaging instruction is received from the operation unit 312. When the input is received, the control unit 200 proceeds directly to step S504, and the OCT 100 captures a tomographic image by scanning a region of the target to be imaged of the examinee eye with the light from the wavelength-swept light source. In step S505, the display control unit 191 displays the tomographic image obtained by imaging, on the display unit 192. Of course, by simultaneously displaying an anterior eye portion image and an SLO image obtained by imaging, efficient and detailed diagnosis can be achieved by images captured from a plurality of side surfaces. Also, when a tomographic image is captured, the tomographic image, a two-dimensional image of the anterior eye portion or the eye fundus, capturing position information of the tomographic image, imaging region information, examinee ID information, imaging time information, imaging screen information, optical path length difference (coherence gate) information, and information about the presence/absence of an eye imaging attachment member are associatively stored in the examinee information storage unit 211.

In step S506, the control unit 200 waits for an analysis instruction by the analysis processing unit 313 with respect to the obtained tomographic image or image group. Like the imaging instruction, the analysis instruction is performed based on the input of the operation unit 312 by the user. When the instruction is received, the analysis processing unit 313 starts analysis processing. Herein, as another embodiment, the analysis processing may be performed without the instruction. In this case, upon detection of the completion of the imaging processing of step S504, the control unit 200 instructs the analysis processing unit 313 to perform analysis processing, and executes step S507. Accordingly, in particular, when it has been known in advance that predetermined analysis processing is performed in medical examination or the like, it is efficient by eliminating unnecessary operations. In step S508, the display control unit 191 displays the analysis processing result on the display unit 192. The processing from the analysis processing instruction to the analysis processing display in steps S506 to S508 may be omitted by the control unit 200 according to settings. This setting is useful in the diagnosis that does not require analysis processing.

In step S509, the control unit 200 waits for a re-imaging instruction. When a re-imaging instruction is received from the operation unit 312, the control unit 200 instructs the OCT 100 to perform re-imaging, and returns to step S502. In another example, the determination unit 310 determines whether there is a need to perform adjustment again. When it is determined that the adjustment is completed, it is efficient to proceed to the imaging processing of step S504.

In step S510, the control unit 200 waits for a termination instruction. When there is a termination instruction, the control unit 200 terminates the imaging. If there is left-right eye switching or a change in the examinee, the control processing returns to step S501.

Figure 6:
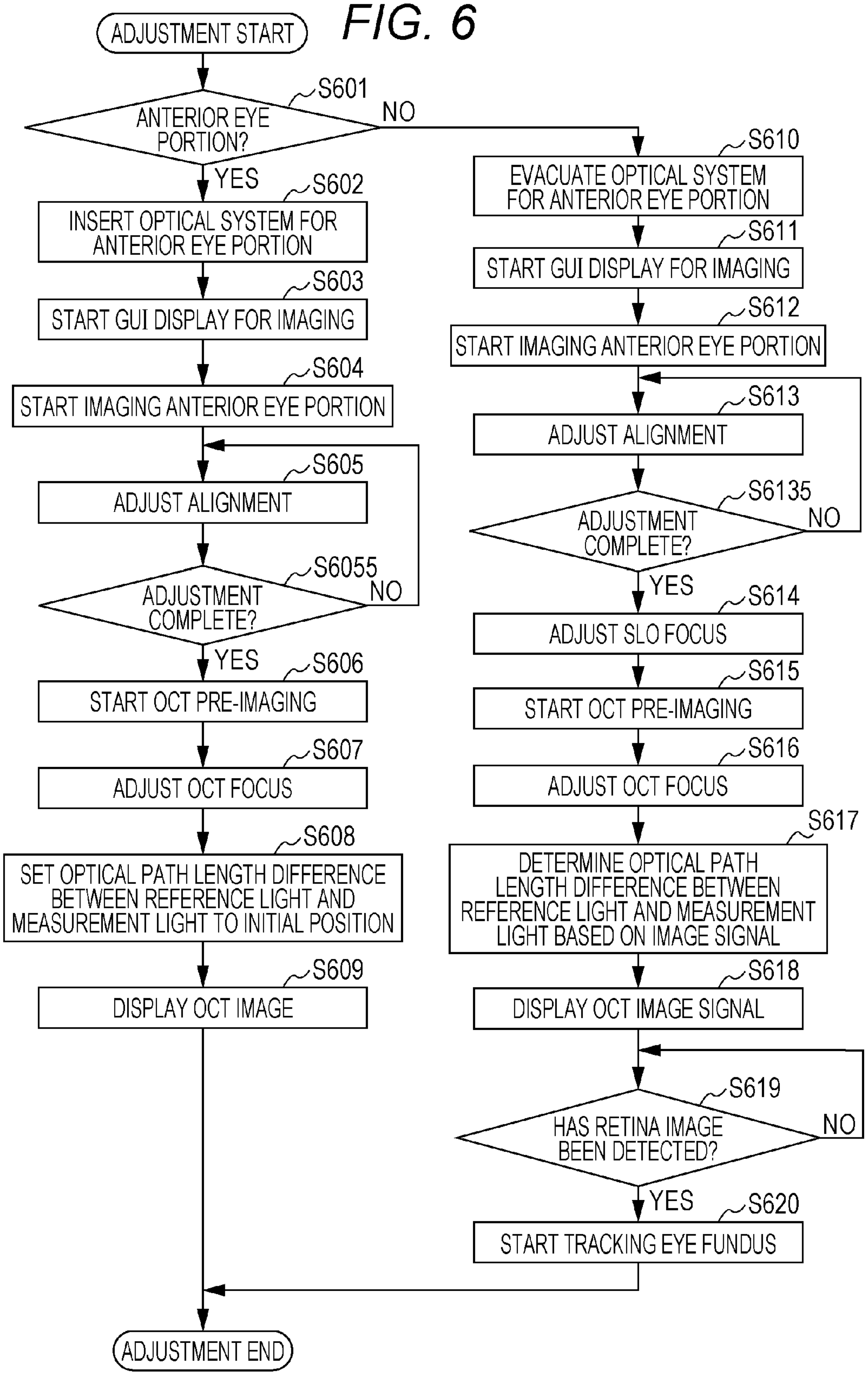
FIG. 6 is a flowchart illustrating an adjustment processing flow before imaging.

An imaging adjustment processing flow according to an embodiment will be described with reference to the flowchart of FIG. 6.

In step S601, based on the information stored in the examinee information storage unit 211, the control unit 200 determines whether an imaging region is an anterior eye portion. The determination may be made based on region information obtained by the region acquiring unit 302, or may be made based on information as to whether the attachment of the anterior eye portion imaging adapter is detected by the adapter detecting unit. Alternatively, by making the determination based on both the region information and the attachment detection information, an imaging region can be set more securely. When it is determined as anterior eye portion imaging, the flow proceeds to step S602, and when it is determined as posterior eye portion imaging, the flow proceeds to step S610.

In step S602, when the anterior eye portion imaging optical system is not disposed on the imaging optical path due to the influence of the previous imaging, the optical system changing unit 304 controls the driving unit to insert the optical system into the imaging optical path.

In step S603, the display control unit 191 starts the display of an anterior eye portion imaging GUI on the display unit 192. For example, information about the imaging region set in step S501 is displayed. As for the GUI displayed on the display unit 192, the display is changed by the display control unit 191 appropriately according to the progress of the adjustment or the imaging. Also, for example, the control unit 200 acquires the adjustment state about a plurality of adjustment items according to the progress of the adjustment. The display control unit 191 displays a tomographic image of the examinee eye, and displays a plurality of acquired adjustment states on the display unit according to a designated imaging mode. The GUI will be described in detail later.

In step S604, the control unit 200 instructs the anterior eye portion image capturing unit 160 to start anterior eye portion imaging. The anterior eye portion imaging is performed in order to automatically or manually adjust the alignment between the anterior eye portion and the OCT apparatus. Also, when a tomographic image of the anterior eye portion is captured, it is used so that the user designates the tomographic imaging position of the anterior eye portion.

In step S605, alignment adjustment is performed by driving the stage unit 207 functioning as the alignment unit. The manual adjustment is performed by moving the stage unit 207 through the operation unit 312 or a joystick (not illustrated). Alternatively, an image of the anterior eye portion may be used to perform automatic alignment by the control unit 200.

In step S6055, the determination unit 310 determines whether the alignment adjustment is completed. When the alignment adjustment is not completed, the control unit 200 drives the stage unit 207 to perform further adjustment. When manual imaging is performed, the determination processing is not performed.

In step S606, the OCT 100 starts OCT pre-imaging. The pre-imaging is to set the imaging condition or the imaging position before actual imaging. Specifically, light is emitted from the light source 101, the XY scanner is driven, an interference light is detected by the balanced receiver 129, and a tomographic image is generated by the signal processing unit 190. At this point, since the focus of the OCT 100 and the coherence gate are not set, a desired tomographic image may not always be obtained.

In step S607, the OCT focus control unit 307 controls the OCT focus position based on an image signal of the tomographic image.

In step S608, the CG control unit 301 sets the optical path length difference between the reference light and the measurement light as the initial position based on the information stored in the examinee information storage unit 211. In this processing, the initial value corresponding to the information stored in the examinee information storage unit 211 is acquired, the coherence gate stage 122 is driven by the driving control unit 180, and the reference mirror 123 is moved to the initial position corresponding to the initial value.

In step S609, the display control unit 191 displays a signal of the tomographic image. Herein, the displayed image data is the image data of the object that is generated by the signal processing unit 190 based on an electric signal obtained by detecting an interference light in the state where the optical path length difference is controlled according to the region.

On the other hand, in the case of posterior eye portion imaging, in step S610, when the anterior eye portion imaging optical system is disposed on the imaging optical path due to the influence of the previous imaging, the optical system changing unit 304 controls the driving unit to evacuate the optical system from the imaging optical path.

In step S611, the display control unit 191 starts the display of a posterior eye portion imaging GUI on the display unit 192.

In step S612, as in step S604, the control unit 200 instructs the anterior eye portion image capturing unit 160 to start anterior eye portion imaging.

In step S613, alignment adjustment is performed in the same way as in step S605.

In step S6135, the determination unit 310 performs the same determination processing as in step S6055.

In step S614 the SLO focus control unit 308 focuses the eye fundus by adjusting the SLO focus position.

In step S615, the OCT 100 starts pre-imaging in the same manner as in step S606.

In step S616, the OCT focus control unit 307 sets the OCT focus position based on the SLO focus position.

In step S617, the CG control unit 301 determines the optical path length difference between the reference light and the measurement light based on the image signal of the tomographic image. The CG control unit 301 searches for the position providing an appropriate optical path length difference while moving the reference mirror 123 by controlling the coherence gate stage 122.

In step S618, the display control unit 191 displays a signal of the tomographic image obtained by the signal processing unit 190.

In step S619, the determination unit 310 determines whether an image of the retina is appropriately obtained. The determination is made based on information as to whether the luminance value of the image is equal to or greater than a threshold value. Alternatively, the determination may be made based on information as to whether an appropriate tomographic image is obtained by pattern matching according to the imaging region.

In step S620, the control unit 200 instructs the SLO 140 to start tracking for compensating the motion of the eye fundus based on the SLO image. The motion information of the eye fundus obtained by the tracking is appropriately input to the control unit 200, and the control unit 200 moves the position of a scanner of the SLO 140 and the OCT 100 to compensate for the motion. When the tracking is started upon adjustment of the SLO focus in step S614, the OCT adjustment can be performed more efficiently.

Figure 7:
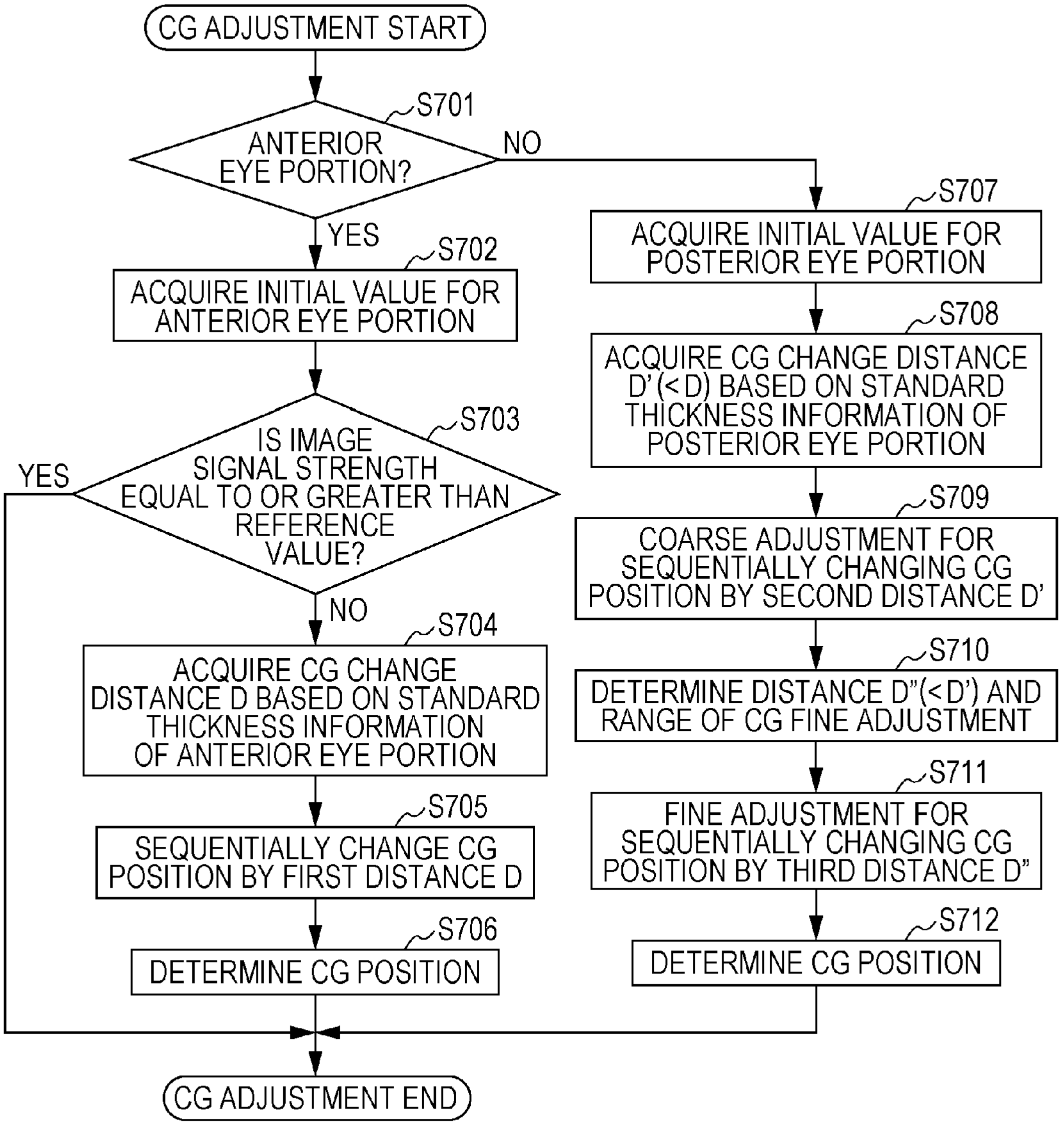
FIG. 7 is a flowchart illustrating a coherence gate adjustment processing flow.

Coherence gate adjustment processing according to an embodiment will be described with reference to the flowchart of FIG. 7. In the control illustrated in FIG. 7, the CG control unit 301 sets an initial value for the anterior eye portion. Only when the standard is not satisfied by the setting, the CG control unit 301 moves the mirror 123 at intervals D to determine the optical path length difference. On the other hand, in the case of posterior eye portion imaging, coarse adjustment is performed to adjust the optical path length difference at intervals D' (<D), fine adjustment is performed to adjust the optical path length difference at intervals D'' (<D'), and the optical path length difference is determined. Accordingly, the efficient adjustment according to the imaging region can be achieved.

In step S701, a determination is made as to whether imaging is anterior eye portion imaging. The determination is the same processing as in step S601.

In step S702, the CG control unit 301 acquires an initial value of a CG adjustment value for the anterior eye portion imaging from the storage unit 309. Herein, when a value obtained by compensating for the value considering the standard thickness information stored in the storage unit 309 based on the working distance measured in the alignment adjustment of step S605 is obtained as the initial value, the adjustment to an appropriate initial value can be performed according to the examinee, the probability of performing the processing subsequent to step S704 can be reduced, and the adjustment can be performed efficiently.

In step S703, the determination unit 310 acquires a tomographic image, which has been obtained with the mirror 123 disposed at the position according to the initial value, from the signal processing unit 190. Then, the determination unit 310 determines whether the luminance value of the tomographic image satisfies the standard. When it is determined that the luminance value of the tomographic image satisfies the standard, the adjustment of a coherence gate is completed.

In step S704, the control setting unit 303 acquires a change interval D of the optical path length difference based on the standard thickness information of the anterior eye portion. The initial value considering the standard thickness information may be pre-stored in the storage unit 309.

In step S705, the CG control unit 301 sequentially changes the position of the mirror 123 at the acquired intervals D. Also, the control unit 200 controls the OCT 100 to capture a tomographic image with the mirror 123 disposed at each position.

In step S706, the determination unit 310 obtains a representative value of the luminance value of the tomographic image corresponding to each position of the mirror. The CG control unit 301 specifies the position of the mirror 123 corresponding to the tomographic image with the greatest representative value, and performs control to move the mirror 123 to the specified position.

On the other hand, in the case of posterior eye portion imaging, in step S707, the CG control unit 301 acquires an initial value of a CG adjustment value for the posterior eye portion imaging from the storage unit 309.

In step S708, the control setting unit 303 acquires a change interval D' of the optical path length difference based on the thickness information of the posterior eye portion. Since the thickness of the posterior eye portion is generally smaller than the thickness of the anterior eye portion, the change interval D' is also smaller than the change interval D in the case of the anterior eye portion imaging. Alternatively, when the change interval D is predetermined, the change interval D' may be set to be smaller than the change interval D.

In step S709, the CG control unit 301 sequentially changes the position of the mirror 123 at the acquired intervals D'. Also, the control unit 200 controls the OCT 100 to capture a tomographic image with the mirror 123 disposed at each position. In parallel with the acquisition of the tomographic image, the determination unit 310 obtains a representative value of the luminance value of the tomographic image corresponding to each position of the mirror. The CG control unit 301 specifies the position of the mirror 123 corresponding to the tomographic image with the greatest representative value.

Herein, when the representative value is greater than a predetermined reference value, the movement of the mirror 123 at that point may be stopped. In this case, the adjustment time can be reduced by moving the mirror sequentially from the vicinity of the initial position acquired in step S708.

The parallel processing of imaging and determination, and the processing of stopping the adjustment upon obtainment of the representative value greater than the reference value may be used for the adjustment in the case of the anterior eye portion imaging.

In step S710, a predetermined range based on the position is set as a search range of fine adjustment. The search range is smaller than the search range of coarse adjustment in step S709. Accordingly, a change interval D'' of the position of the mirror 123 for searching for the search range is smaller than the change interval D', and is acquired by the control setting unit 303.

In step S711, the CG control unit 301 sequentially changes the position of the mirror 123 at the acquired intervals D''. Also, the control unit 200 controls the OCT 100 to capture a tomographic image with the mirror 123 disposed at each position.

In step S712, the determination unit 310 obtains a representative value of the luminance value of the tomographic image corresponding to each position of the mirror. The CG control unit 301 determines the position of the mirror 123 corresponding to the tomographic image with the greatest representative value.

Also, by performing the adjustment of a coherence gate position at predetermined intervals even after the above adjustment, the influence on the image quality by the optical path length difference change between the adjustment end point and the imaging start point can be reduced.

Figure 8:
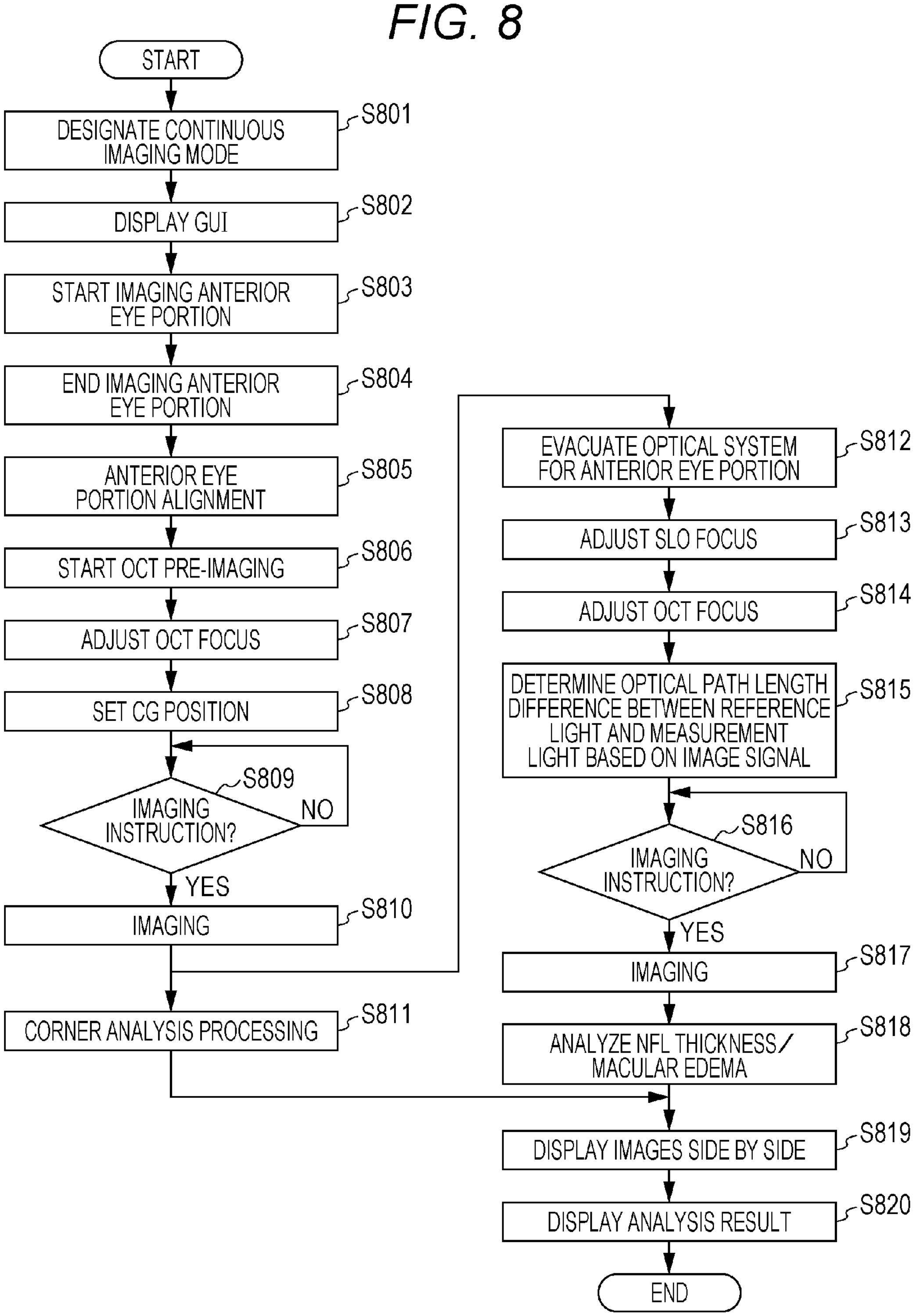
FIG. 8 is a flowchart illustrating an imaging processing flow in a continuous imaging mode.

Adjustment processing in the case of instruction of a continuous imaging mode will be described with reference to the flowchart of FIG. 8. The processing of steps S803 to S810 corresponds to the processing of steps S604, S605, S606, S607, S608, steps S503 and S504 of FIGS. 6 and 5. Also, the processing of steps S813, S814, S816 and S817 corresponds to the processing of steps S614, S616, S503 and S504.

In step S801, the mode designating unit 311 designates a continuous imaging mode according to an operation input of the user. Herein, the continuous imaging mode is an imaging mode for imaging a plurality of imaging regions continuously. When a target to be imaged is an eye portion, there is, for example, an imaging mode for imaging both the anterior eye portion and the posterior eye portion. In this imaging mode, after completion of the imaging of one of the anterior eye portion and the posterior eye portion, at least a portion of imaging preparation of the other one is started. In this case, there is a case where the imaging screen is shifted automatically according to the imaging mode, and a case where the imaging screen capable of imaging both the anterior eye portion and the posterior eye portion is displayed. In the imaging mode for imaging both the anterior eye portion and the posterior eye portion, the imaging screen is set based on the information stored in the examinee information storage unit 211.

In step S802, the display control unit 191 starts the display control of a continuous imaging GUI. In the case of continuous imaging, the display control unit 191 displays one imaging GUI before the one imaging, and displays the next imaging GUI upon termination of the one imaging. Also, regardless of which imaging adjustment is being performed, the continuous imaging mode is displayed as the imaging mode. Alternatively, when the completed imaging region or imaging mode and the next uncompleted imaging region or imaging mode are displayed, the order of imaging in the case of performing a plurality of imaging operations (particularly, three or more continuous imaging operations) is recognized by the user, thus making it possible to reduce the possibility of erroneous imaging.

In step S808, the CG control unit 301 adjusts the optical path length difference between the reference light and the measurement light. The adjustment result is stored in the storage unit 309 and the examinee information storage unit 211 by the control unit 200. Also, when a tomographic image is captured, the tomographic image, a two-dimensional image of the anterior eye portion or the eye fundus, capturing position information of the tomographic image, imaging region information, examinee ID information, imaging time information, imaging screen information, optical path length difference (coherence gate) information, and information about the presence/absence of an eye imaging attachment member are associatively stored in the examinee information storage unit 211.

In step S811, the analysis processing unit 313 analyzes a corner based on the tomographic image of the anterior eye portion that has been imaged. Besides, each cornea thickness may be analyzed. The analysis processing is performed by using, for example, the GPU of the control unit 200. Also, the signal processing unit 190 performs the analysis processing of the tomographic image obtained by tomography of the anterior eye portion in parallel with the next imaging to be analyzed, before termination of posterior eye portion tomography after anterior eye portion tomography, thereby making it possible to reduce the delay time from the imaging to the display of the analysis processing result.

The adjustment processing of steps S812 to S815 for posterior eye portion imaging is automatically shifted by the control unit 200 upon completion of the imaging of step S810. Also, in the case of the continuous imaging mode, since anterior eye portion alignment is completed in step S805, the anterior eye portion alignment is skipped and control is performed.

In step S812, the optical system changing unit 304 evacuates the optical system upon completion of the imaging in the same manner as in step S610.

In step S813, the SLO focus control unit 308 starts the adjustment of the focus position of the measurement light of the SLO 140 upon completion of the imaging. In step S814, the OCT focus control unit 307 starts the adjustment of the focus position of the measurement light of the OCT 100 upon completion of the imaging. In the case of the posterior eye portion, since a signal by the OCT 100 is weak, a lookup table representing the correspondence relation between the SLO focus position and the OCT focus lens position is stored in the storage unit 309, and the OCT focus position is controlled based on the SLO focus information.

In step S815, the CG control unit 301 performs CG adjustment upon completion of the imaging. Herein, the CG control unit 301 acquires an optical path length difference value for anterior eye portion imaging, which has been stored in step S808, from any one of the storage unit 309 and the examinee information storage unit 211, and compares the value with a standard value. The initial value used in step S815 is changed from a predetermined value by the difference from the standard value.

In step S818, the analysis processing unit 313 analyzes the tomographic image of the posterior eye portion. In the analysis processing, the thickness of each layer of the retina and lesion such as macular edema are detected. Herein, when the GPU is used to perform the analysis processing, the analysis processing of step S818 may be performed upon completion of the analysis processing of step S811.

In step S819, the display control unit 191 displays the obtained tomographic images side by side. By displaying the obtained tomographic images side by side, it is possible to improve the diagnosis efficiency of a disease such as diabetes, in which an abnormality appears in both regions such as the thickness of the retinal layer of the posterior eye portion and the corner of the anterior eye portion. Herein, when the image display processing is performed before completion of the analysis process of any one of steps S811 and S818, diagnosis can be performed by the image until derivation of the analysis processing result so that the user does not wait in vain.

In step S820, the display control unit 191 displays the obtained analysis result on the display unit 192.

By the above processing, continuous imaging can be executed efficiently.

Figure 9:
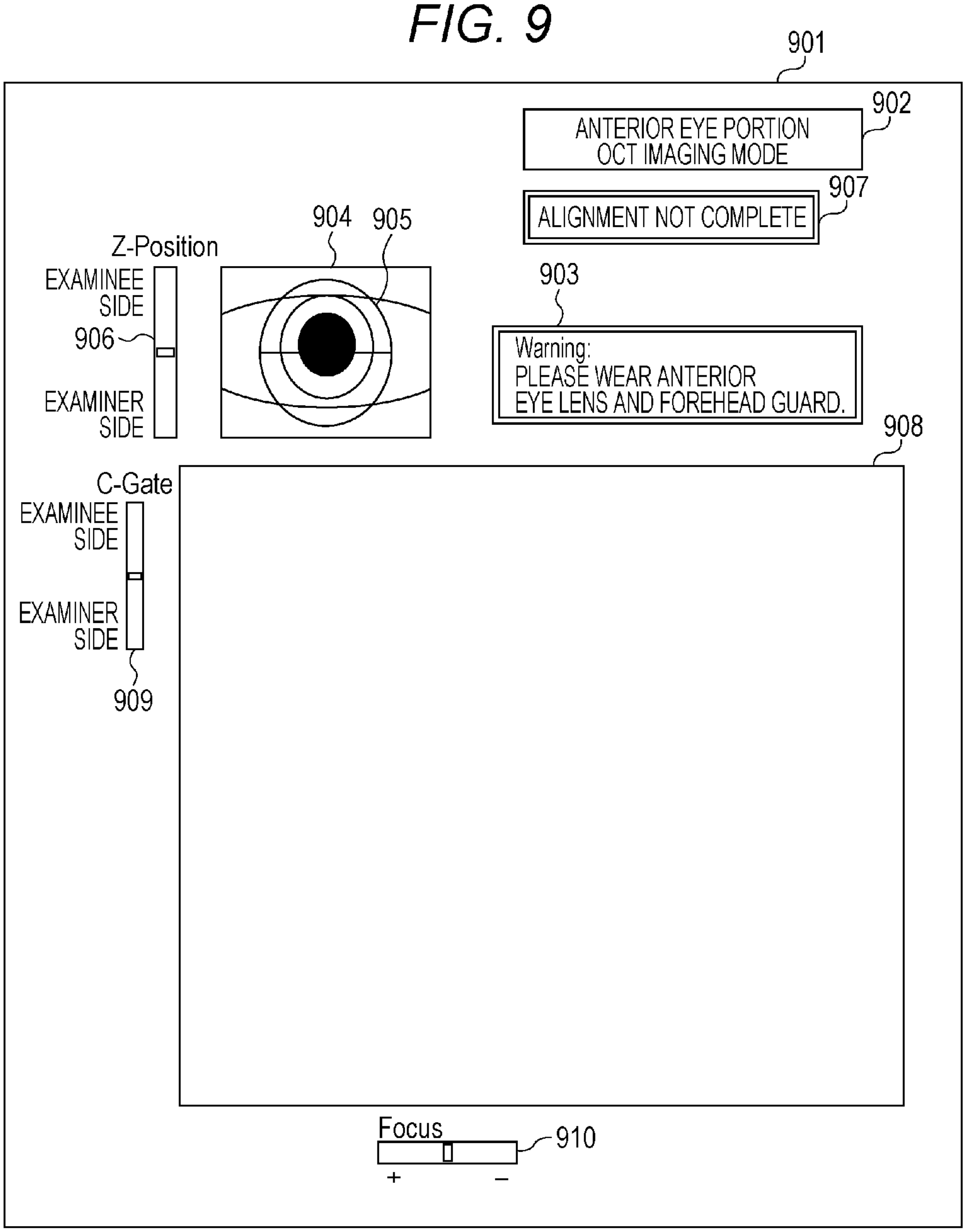
FIG. 9 is a diagram illustrating an example of an imaging screen in an anterior eye portion OCT imaging mode.

FIG. 9 is a diagram illustrating an example of an anterior eye portion imaging GUI set according to the information stored in the examinee information storage unit 211. A display screen 901 acquires and displays imaging support information, imaging setting information, and an image being captured, in real time. The display screen 901 is displayed on the display unit 192 under the control of the display control unit 191.

An area 902 is a display area for displaying an imaging mode designated by the mode designating unit 311. In the case of an anterior eye portion imaging mode, the text of "Anterior Eye Portion OCT Mode" is displayed in the area 902. Alternatively, not a text, but an icon may be used to display an imaging region such that the imaging region is emphasized in an eye portion image.

An area 903 is a display area for displaying an adjustment state of an adjustment item according to an imaging mode. As illustrated in FIG. 9, as adjustment items peculiar to the anterior eye portion imaging mode, information representing the adjustment states of an anterior eye lens and a forehead guard is displayed.

An area 907 is a display area for displaying an adjustment state of an adjustment item common to a plurality of imaging modes. In FIG. 9, the text representing "alignment incompletion" is displayed.

Unlike the area 902, the area 903 and the area 907 are surrounded by a double frame border. This represents adjustment incompletion. On the other hand, when the representation of completion is displayed with respect to an adjustment item completed in adjustment, the areas are surrounded by a typical frame border as in the area 902. In this manner, the display control unit 191 displays a plurality of adjustment states in display modes representing an adjustment item completed in adjustment for anterior eye portion imaging and an adjustment item uncompleted in the adjustment, and displays the uncompleted adjustment item emphatically. By the emphasized display, the user can recognize the meaning of adjustment incompletion.

In addition, the text of "Warning" is displayed in the area 903. The text of "Warning" is displayed when the display control unit 191 determines that there is a disagreement between the display mode information displayed in the area 902 and the state of the adjustment item. In the case of anterior eye portion imaging, position alignment cannot be accurately performed unless an adapter unit such as an anterior eye lens or a forehead guard is attached in advance in order to adjust the working distance and the optical system. In this manner, the display control unit 191 displays a plurality of adjustment states in display modes according to appropriated imaging modes, and attaches a warning indication to the adjustment state disagreeing with the imaging mode. Accordingly, the user can be strongly urged to perform adjustment.

An anterior eye observation area 904 displays an image 905 of the anterior eye portion obtained by the anterior eye portion image capturing unit 160.

An alignment slider 906 disposed in the vicinity of the anterior eye observation area 904 is a GUI for manually adjusting the Z-direction position of an optical head with respect to the examinee eye according to user operation. When the user moves the alignment slider 906 through the operation unit 312, the driving control unit 180 moves the stage unit 207 in the Z direction along the moving direction. By clicking an arbitrary point on the anterior eye observation area 904 with a mouse, an optical head 208 is moved by an XYZ table (not illustrated) such that the point is centered on the screen, position alignment between the optical head and the examinee eye is performed.

An area 908 is a display area for checking a tomographic image acquired by the OCT 100.

A CG slider 909 is a GUI for manually adjusting the position of a coherence gate of the OCT 100 according to user operation. Herein, the initial position is set according to the information stored in the examinee information storage unit 211. Also, when the user moves the CG slider 909 through the operation unit 312, the CG control unit 301 drives the coherence gate stage 122 through the driving control unit 180 along the moving direction, and moves the mirror 123.

A focus slider 910 is a GUI for manually adjusting the focus position of the OCT 100 according to user operation. For focus adjustment, the OCT focus control unit 307 instructs the driving control unit 180 to move the focus lens in the illustrated direction in order to perform focusing on the eye fundus. When the user moves the focus slider 910 through the operation unit 312, the OCT focus control unit 307 controls the driving control unit 180 according to the moving direction and changes the position of the focus lens.

Figure 10:
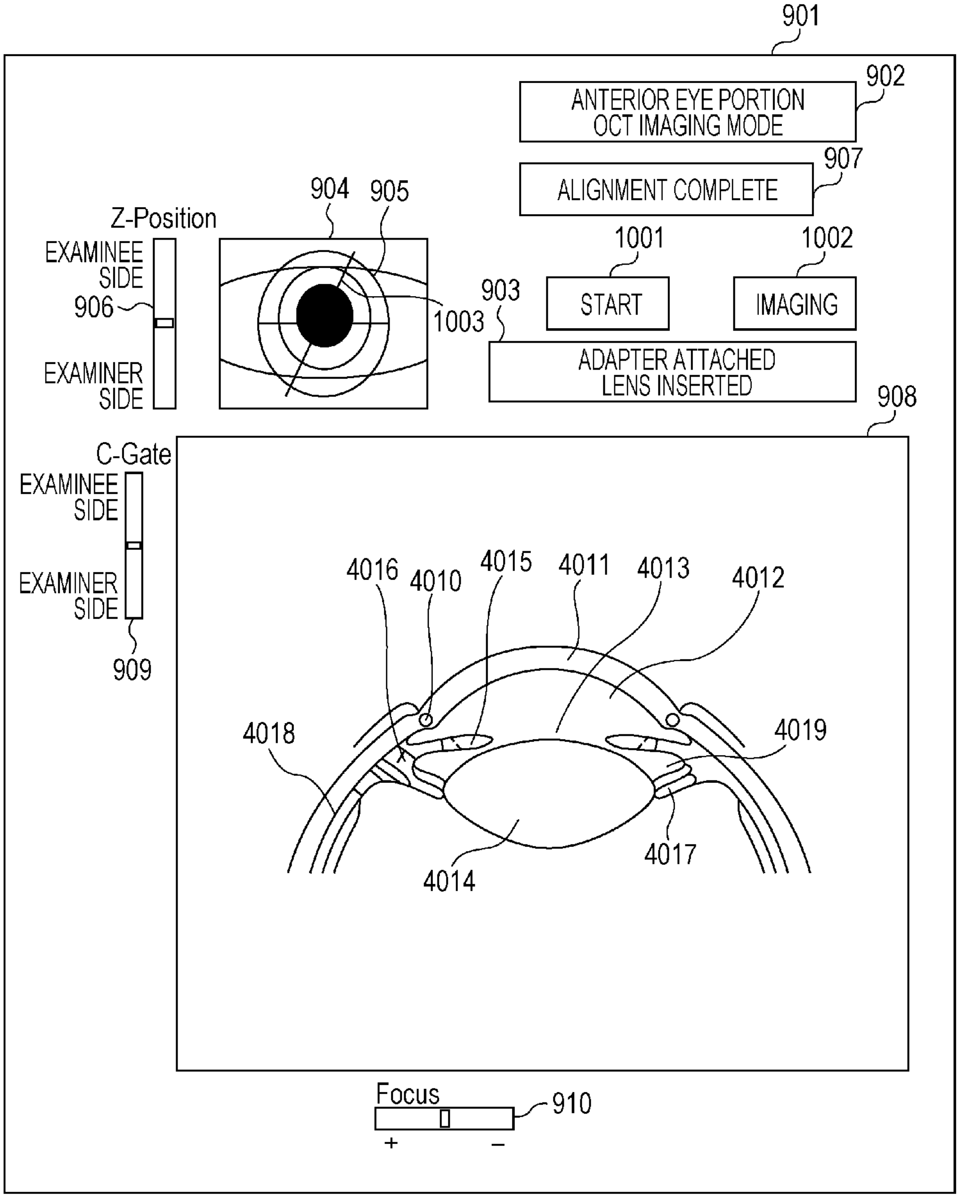
FIG. 10 is a diagram illustrating another example of an imaging screen in the case of anterior eye portion imaging.

FIG. 10 is a diagram illustrating other examples of an anterior eye portion imaging GUI set according to the information stored in the examinee information storage unit 211. In the state illustrated in FIG. 10, information representing alignment completion is displayed in the area 907 while being surrounded by a single frame border. Information representing appropriate setting of the adapter unit by the text of "Adapter Attached, Lens Inserted" is displayed in the area 903 while being surrounded by a single frame border. A tomographic image of the anterior eye portion is displayed in the area 908. A line segment 1003 is displayed in a superimposed manner on the image 905 of the anterior eye portion in the anterior eye observation area 904. The line segment 1003 represents a scan position (imaging range) corresponding to the tomographic image displayed in the area 908. The user can freely set the position of the line segment 1003 through the operation unit 312. The scan of the present imaging may be performed at the set final position of the line segment 1003.

In the state illustrated in FIG. 10, it has been determined by the determination unit 310 that imaging is possible. In this case, upon determination of the possibility of imaging, the display control unit 191 displays an imaging button 1002.

When various adjustments are completed, the imaging button 1002 is pressed to perform desired imaging. Also, when a tomographic image is captured, the tomographic image, a two-dimensional image of the anterior eye portion, capturing position information of the tomographic image, imaging region information, examinee ID information, imaging time information, imaging screen information, optical path length difference (coherence gate) information, and information about the presence/absence of an eye imaging attachment member are associatively stored in the examinee information storage unit 211.

Besides, by pressing a start button 1001, pre-capturing of a tomographic image is started, and an examinee eye image is displayed in the area 908 in real time.

FIG. 11 is a diagram illustrating an example of a screen in the case where a posterior eye portion imaging GUI set according to the information stored in the examinee information storage unit 211 is displayed on the display screen 901. The same portions as in FIGS. 9 and 10 will not be described herein.

An imaging mode designated by the user through the text of "Eye Fundus OCT Mode" is displayed in the area 902. In the area 903, the text representing OCT focus incompletion is displayed while being surrounded by a double frame border representing adjustment incompletion. A GUI in the case where an automatic adjustment mode is not turned off is displayed. In this case, the representation of alignment adjustment completion is not displayed in the area 907 in order to improve the operability of the user and the visibility of information.

FIG. 12 is a diagram illustrating an example of a posterior eye portion imaging GUI set according to the information stored in the examinee information storage unit 211. In addition, after completion of the imaging, when a tomographic image is captured, the tomographic image, a two-dimensional image of the anterior eye portion or the eye fundus, capturing position information of the tomographic image, imaging region information, examinee ID information, imaging time information, imaging screen information, optical path length difference (coherence gate) information, and information about the presence/absence of an eye imaging attachment member are associatively stored in the examinee information storage unit 211.

An area 1201 is a display area for displaying a two-dimensional image of the eye fundus acquired by the SLO 140.

As in FIG. 11, in FIG. 12, a GUI in the case where an automatic adjustment mode is not turned off is displayed. In this case, the representation of alignment adjustment completion is not displayed, in order to improve the operability for the user and the visibility of information. In addition, in FIG. 12, the tomographic image of the eye fundus is displayed, and there is no need to display imaging region information. Therefore, the display of the area 902 is deleted on the screen.

FIG. 13 is a diagram illustrating an example of a display screen of the analysis processing result in the case where continuous imaging is selected according to the information stored in the examinee information storage unit 211. Also, the display screen can be used even when the anterior eye portion and the posterior eye portion of the same examinee eye are imaged.

An area 1300 is a display area for displaying a tomographic image of the anterior eye portion.

A plane image 1301 of the anterior eye portion obtained by the imaging unit 160 is displayed on an area 1302. In the area 1302, a scan position corresponding to the tomographic image of the anterior eye portion is represented by a line segment 1309 in a dotted line. From the viewpoint of visibility, the display mode is such that the length of the line segment and scan range do not agree with each other. Of course, when only the position corresponding to the scan range is represented by a solid line, the correspondence relation with the imaging range can be easily understood.

An area 1304 represents the graph of a corner size as one of the results obtained by analyzing a tomographic image of the anterior eye portion by the analysis processing unit 313. In the graph, the vertical axis represents a corner size. As for the corner size obtained by analysis, the angular component of polar coordinates around the pupil is represented as a position on the horizontal axis. A line segment 1305 corresponds to the imaging position of the tomographic image displayed in the area 1300. Also, it corresponds to a line segment 1309 representing the scan position of the area 1302. The user can operate the operation unit 312 to change the position of any one of the tomographic image, the line segment 1309 and the line segment 1305. Accordingly, the other images or lines are moved to the corresponding positions in conjunction with each other. Accordingly, the tomographic image and the corner value can be compared and referred to.

A tomographic image of the posterior eye portion is displayed in an area 1306. A plane image of the eye fundus captured by the SLO is displayed in an area 1307. A layer thickness map of a specific layer may be displayed in a superimposed manner on an image of the eye fundus in the area 1307. Based on the operation of the operation unit 312 by the user, the display control unit 191 appropriately selects the display of the layer thickness map and the layer as the display target from the analysis result of the storage unit 309 prior to display. A graph representing the layer thickness of a specific layer in the tomographic image displayed in the area 1306 is displayed in an area 1308. In the graph, the vertical axis represents a layer thickness, and the horizontal axis represents the position of a tomographic image in the B scan direction. In the area 1307, a line segment corresponding to the range and the scan position of the tomographic image displayed by a line segment 1310 in the area 1306 is drawn. Based on the input from the operation unit 312 by the user, the display control unit 191 selects a layer as a display target in the area 1307 and the area 1308.

When the user operates any one of the position of the line segment 1310, the tomographic image and the layer thickness as the display target through the operation unit 312, other information is changed in conjunction. Accordingly, the scan position, the tomographic image, the layer thickness map, and the graph of the layer thickness in a specific tomographic image can be easily performed while retaining the correspondence relation.

In addition, by collectively displaying the analysis result and the image of the anterior eye portion and the analysis result and the image of the posterior eye portion, the integrated comparison between the abnormality of the anterior eye portion and the abnormality of the posterior eye portion with respect to a specific disease is facilitated.

[Display Screen]

Figure 14:
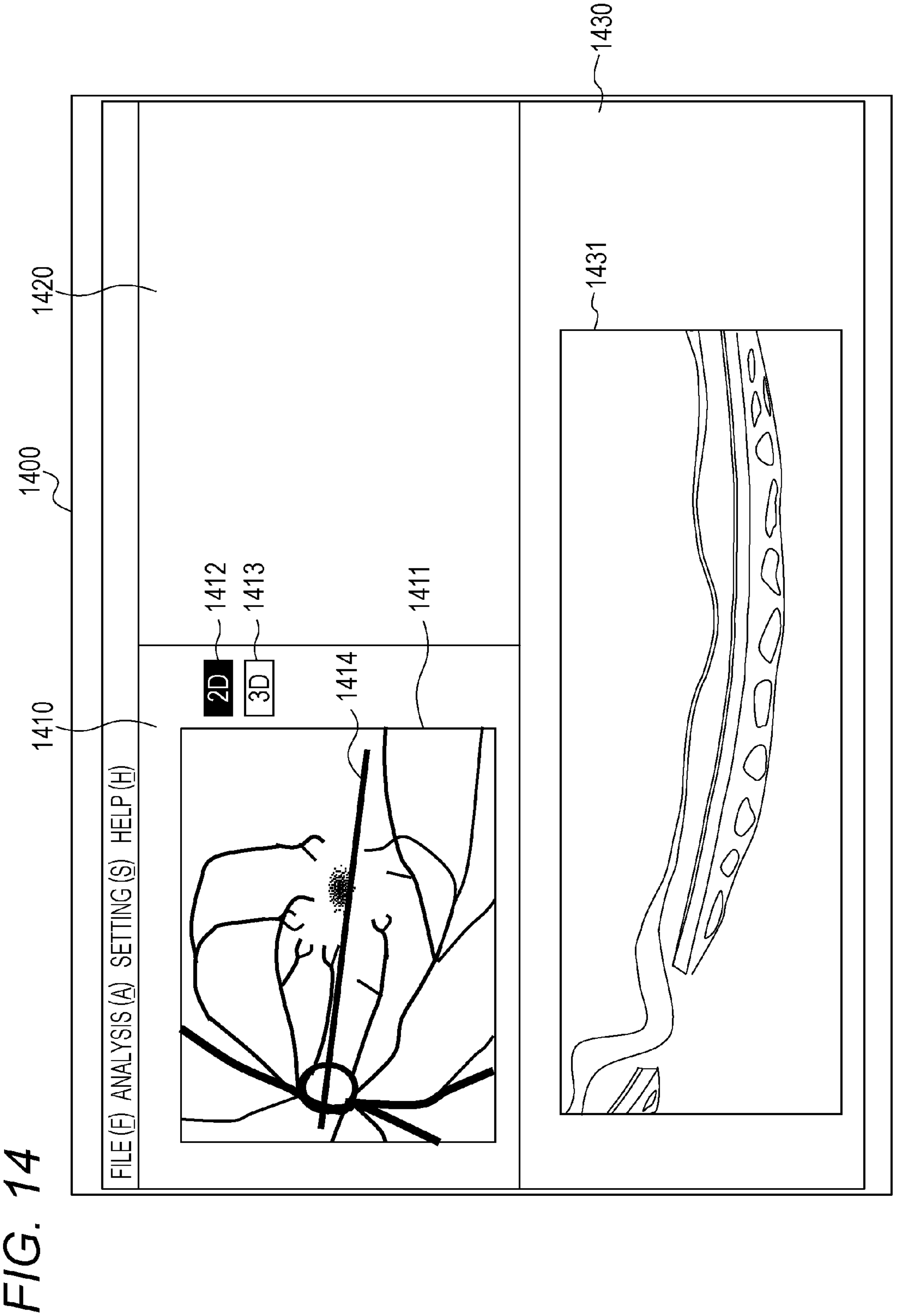
FIG. 14 illustrates another display example in a display unit.

FIG. 14 is a diagram illustrating an example of an imaging screen in the display unit 192 that is set according to the information stored in the examinee information storage unit 211 according to the present embodiment. In FIG. 14, a tomographic image 1431 captured in a 2D image capturing mode is displayed in an area 1430.

The OCT 100 has a deep imaging area. Therefore, in the present embodiment, a tomographic image at a predetermined depth from the position of a coherence gate (the length in the vertical direction of the drawing) is cut out and displayed. Also, although a display area 1431 of the tomographic image is located under an area 1411 in which an eye fundus image is displayed, the area 1431 may be located over the area 1411. By displaying a tomographic image in the area 1431 over or under the area 1411, a tomographic image with a wide angle of view can be displayed without reduction, and thus the tomographic image can be easily observed. Also, apparatus information, examinee information and the like are displayed in an area 1420. In addition, after completion of the imaging, when a tomographic image is captured, the tomographic image, a two-dimensional image of the eye fundus, capturing position information of the tomographic image, imaging region information, examinee ID information, imaging time information, imaging screen information, optical path length difference (coherence gate) information, and information about the presence/absence of an eye imaging attachment member are associatively stored in the examinee information storage unit 211.

As described above, according to the present embodiment, a tomographic image with a wide angle of view acquired by SS-OCT and the like can be efficiently presented. Also, when the entire tomographic image cannot be displayed in the tomographic image display area prepared, since the tomographic image is displayed by expanding the display area, the tomographic image can be displayed without degradation of resolution. In addition, when the entire tomographic image cannot be displayed in the tomographic image display area prepared, since the tomographic image is displayed by scrolling the area, a desired portion of the tomographic image to be observed can be displayed.

For example, in SS-OCT, the depth-direction imaging range can be increased as compared to the case of conventional OCT, it can be used for tomography of not only a retina but also an anterior eye portion, for example.

Figure 15:
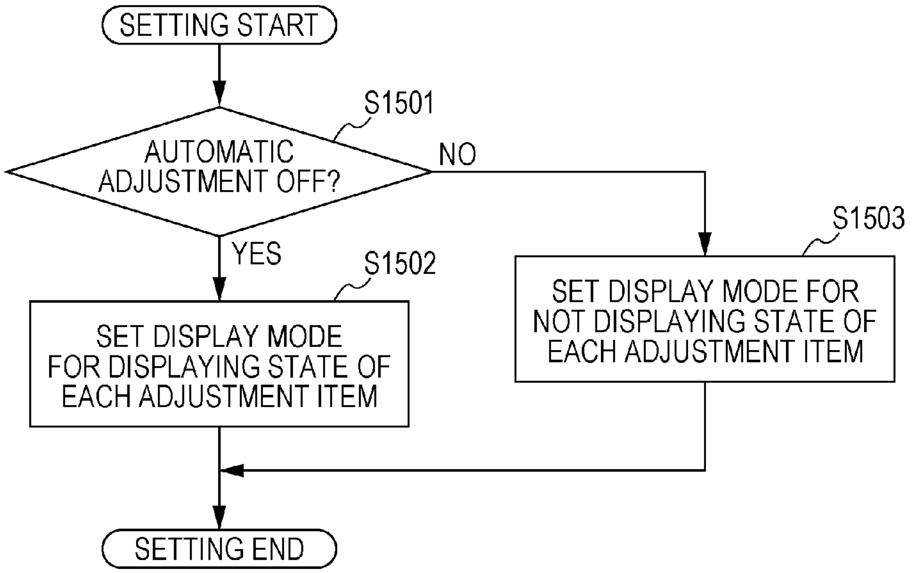
FIG. 15 is a flowchart illustrating a display mode setting processing flow.

Automatic adjustment setting will be described with reference to the flowchart of FIG. 15.

In step S1501, the control setting unit 303 determines whether automatic adjustment is turned off. The designation of automatic adjustment is performed by the mode designating unit 311 based on the operation input from the operation unit 312. When it is determined that automatic adjustment is turned off, the flow proceeds to step S1502, and when automatic adjustment is not turned off, the flow proceeds to step S1503.

In step S1502, when automatic adjustment is turned off, the control setting unit 303 performs control to set a display mode displaying information representing adjustment completion with respect to an adjustment item for setting completed in adjustment as a determination result of the determination unit 310. The control setting unit 303 sets the display mode with respect to the display control unit 191.

In step S1503, the control setting unit 303 sets a display mode not displaying information representing adjustment completion with respect to an adjustment item completed in adjustment. The control setting unit 303 sets the display mode with respect to the display control unit 191. Since it is meaningless to notify the adjustment state of a completed adjustment item to the user, the efficient use of the screen area can be achieved and the visibility of information can be improved.

When the mode designating unit 311 turns off automatic adjustment of a focus and a coherence gate, the control setting unit 303 instructs the stage unit 207 functioning as the alignment unit, the adapter detecting unit illustrated FIG. 2 (FIGS. 2A-2B), the focus control unit 307, and the CG control unit 301 not to perform automatic adjustment. In addition, the control setting unit 303 can set whether to automatically perform a plurality of adjustment items separately. Also, in this case, while performing control not to perform automatic adjustment, the determination as to the completion/incompletion of adjustment may not be terminated. Of course, the control setting unit 303 may instruct the determination unit 310 not to perform the determination processing.

Besides, an appropriate combination of the above-described embodiments is also included in the embodiments of the present invention. Also, implementation of a portion of the present invention in cooperation with a program and hardware is also included in the embodiments of the present invention. In an embodiment using a program, a program corresponding to the processing illustrated in FIGS. 5 to 8 and 15, and a program corresponding to the display screen illustrated in FIGS. 9 to 14 are stored in the program storage unit 309, and the CPU develops the program on a RAM and executes instructions included in the program for implementation.

The above embodiment is merely an example of the embodiments of the present invention, and the scope of the present invention is not limited to the above-described embodiment.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-084969, filed Apr. 3, 2012, which is hereby incorporated by reference herein in its entirety.

What is claimed is:

1. An optical coherence tomography apparatus for obtaining a tomographic image from an interference light between a reference light and a measurement light having passed through an object, the optical coherence tomography apparatus comprising:

a detection unit configured to detect the presence/absence of an anterior eye imaging attachment member of the optical coherence tomography apparatus; and a control unit configured to display an imaging screen for anterior imaging or for fundus imaging based on a detection result by the detection unit.

2. The optical coherence tomography apparatus according to claim 1, wherein the anterior eye imaging attachment member is any one of an anterior eye imaging lens and a chin receiving member.

3. The optical coherence tomography apparatus according to claim 1, further comprising a storage unit configured to store information about an optical path length difference between the reference light and the measurement light, wherein the control unit changes the imaging screen according to the information about the optical path length difference stored in the storage unit.

4. The optical coherence tomography apparatus according to claim 1, further comprising:

a storage unit configured to store information about an optical path length difference between the reference light and the measurement light; and a setting unit configured to set a coherence gate according to the information about the optical path length difference stored in the storage unit, wherein the control unit displays information representing the optical path length difference.

5. The optical coherence tomography apparatus according to claim 4, wherein the storage unit stores imaging position information of the tomographic image when the object is imaged, and the position information is displayed on the imaging screen when the object is imaged again.

6. The optical coherence tomography apparatus according to claim 4, wherein the control unit controls an optical path length difference of a predetermined imaging region by two-stage adjustment of coarse adjustment and fine adjustment.

7. The optical coherence tomography apparatus according to claim 4, further comprising:

a changing unit configured to change an optical path length difference displayed on the imaging screen; and a signal processing unit configured to generate image data of the object based on an electric signal obtained by detecting the interference light by the changed optical path length difference, wherein the control unit displays the tomographic image obtained by the signal processing unit on the imaging screen.

8. The optical coherence tomography apparatus according to claim 7, further comprising:

a determination unit configured to determine whether the image data obtained by the signal processing unit satisfies a predetermined standard, wherein, when the determination unit determines that the predetermined standard is not satisfied, the control unit controls the optical path length difference based on a signal of the interference light obtained while sequentially changing the optical path length difference.

9. The optical coherence tomography apparatus according to claim 8, wherein the determination unit determines whether a representative value of a pixel value of the image data is equal to or greater than a predetermined threshold value.

10. The optical coherence tomography apparatus according to clam 1, wherein the imaging screen for the anterior imaging and the imaging screen for the fundus imaging are different in size of an area where the tomographic image is displayed.

11. The optical coherence tomography apparatus according to claim 1, further comprising a changing unit configured to change an optical path length difference displayed on the imaging screen, wherein the control unit is configured to control, based on a change of the optical path length difference by the changing unit, a reference light path length at a first interval or a second interval smaller than the first interval.

12. The optical coherence tomography apparatus according to claim 11, wherein the control unit is configured to control the reference light path length at the first interval in a case where the anterior eye imaging attachment member is present, and to control the reference light path length at the second interval in a case where the anterior eye imaging attachment member is not present.

13. A control method for an optical coherence tomography apparatus for obtaining a tomographic image from an interference light between a reference light and a measurement light having passed through an object, the control method comprising:

detecting the presence/absence of an anterior eye imaging attachment member of the optical coherence tomography apparatus; and displaying an imaging screen for anterior imaging or for fundus imaging based on a detection result in the detecting step.

14. A storage medium having stored a computer program for executing the control method according to claim 13.

15. An optical coherence tomography apparatus comprising:

a light source;

a branching unit configured to branch a light from the light source into a reference optical system and an imaging optical system;

a signal processing unit configured to obtain a tomographic image from an interference light between a return light of the reference optical system and a measurement light having passed through an object through the imaging optical system, while changing an wavelength of the light source;

a detection unit configured to detect the presence/absence of an anterior eye imaging attachment member of the optical coherence tomography apparatus; and a control unit configured to display an imaging screen for anterior imaging or for fundus imaging based on a detection result by the detection unit.

16. An optical coherence tomography apparatus for obtaining a tomographic image from an interference light between a reference light and a measurement light having passed through an object, the optical coherence tomography apparatus comprising:

a detection unit configured to detect the presence/absence of an additional lens of the optical coherence tomography apparatus; and a control unit configured to display an imaging screen for anterior imaging or for fundus imaging based on a detection result by the detection unit.

17. The optical coherence tomography apparatus according to clam 16, wherein the imaging screen for the anterior imaging and the imaging screen for the fundus imaging are different in size of an area where the tomographic image is displayed.

18. The optical coherence tomography apparatus according to claim 16, further comprising a changing unit configured to change an optical path length difference displayed on the imaging screen, wherein the control unit is configured to control, based on a change of the optical path length difference by the changing unit, a reference light path length at a first interval or a second interval smaller than the first interval.

19. The optical coherence tomography apparatus according to claim 18, wherein the control unit is configured to control the reference light path length at the first interval in a case where the additional lens is present, and to control the reference light path length at the second interval in a case where the additional lens is not present.

20. A control method for an optical coherence tomography apparatus for obtaining a tomographic image from an interference light between a reference light and a measurement light having passed through an object, the control method comprising:

detecting the presence/absence of an additional lens of the optical coherence tomography apparatus; and displaying an imaging screen for anterior imaging or for fundus imaging based on a detection result by the detection unit.

* * * * *